United States Patent
Larson

(10) Patent No.: US 10,675,296 B2
(45) Date of Patent: Jun. 9, 2020

(54) COMPOSITIONS COMPRISING AN RNA POLYMERASE INHIBITOR AND CYCLODEXTRIN FOR TREATING VIRAL INFECTIONS

(71) Applicant: Gilead Sciences, Inc., Foster City, CA (US)

(72) Inventor: Nate Larson, Saint George, UT (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 16/031,620

(22) Filed: Jul. 10, 2018

(65) Prior Publication Data

US 2019/0083525 A1    Mar. 21, 2019

Related U.S. Application Data

(60) Provisional application No. 62/530,971, filed on Jul. 11, 2017.

(51) Int. Cl.
| | | |
|---|---|---|
| *A61K 31/724* | (2006.01) | |
| *A61K 47/40* | (2006.01) | |
| *A61K 9/19* | (2006.01) | |
| *A61K 47/69* | (2017.01) | |
| *A61P 31/12* | (2006.01) | |
| *A61K 31/683* | (2006.01) | |
| *A61K 9/00* | (2006.01) | |

(52) U.S. Cl.
CPC .......... *A61K 31/724* (2013.01); *A61K 9/0019* (2013.01); *A61K 9/19* (2013.01); *A61K 31/683* (2013.01); *A61K 47/40* (2013.01); *A61K 47/6951* (2017.08); *A61P 31/12* (2018.01)

(58) Field of Classification Search
CPC ................ A61K 31/683; A61K 31/724; A61K 47/6951; A61K 47/40; A61K 9/19; A61P 31/12
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,476,030 B1 | 11/2002 | Carling et al. | |
| 6,656,915 B1 | 12/2003 | Bantia et al. | |
| 6,909,011 B2 | 6/2005 | Skranc et al. | |
| 7,105,493 B2 | 9/2006 | Sommadossi et al. | |
| 7,125,855 B2 | 10/2006 | Bhat et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |
| 7,390,791 B2 | 6/2008 | Becker et al. | |
| 7,429,571 B2 | 9/2008 | Chand et al. | |
| 7,514,410 B2 | 4/2009 | Babu et al. | |
| 7,560,434 B2 | 7/2009 | Babu et al. | |
| 7,598,230 B2 | 10/2009 | Cook et al. | |
| 7,608,597 B2 | 10/2009 | Sommadossi et al. | |
| 7,713,941 B2 | 5/2010 | Cook et al. | |
| 7,803,788 B2 | 9/2010 | Becker et al. | |
| 7,807,653 B2 | 10/2010 | Cook et al. | |
| 7,842,672 B2 | 11/2010 | Boojamra et al. | |
| 7,951,787 B2 | 5/2011 | McGuigan | |
| 7,973,013 B2 | 7/2011 | Cho et al. | |
| 7,994,139 B2 | 8/2011 | Babu et al. | |
| 8,008,264 B2 | 8/2011 | Butler et al. | |
| 8,012,941 B2 | 9/2011 | Cho et al. | |
| 8,012,942 B2 | 9/2011 | Butler et al. | |
| 8,071,568 B2 | 12/2011 | Narjes et al. | |
| 8,119,607 B2 | 2/2012 | Francom et al. | |
| 8,242,085 B2 | 8/2012 | Babu et al. | |
| 8,318,682 B2 | 11/2012 | Butler et al. | |
| 8,415,308 B2 | 4/2013 | Cho et al. | |
| 8,455,451 B2 | 6/2013 | Cho et al. | |
| 8,853,171 B2 | 10/2014 | Butler et al. | |
| 8,871,737 B2 | 10/2014 | Smith et al. | |
| 8,889,159 B2 | 11/2014 | Clearly et al. | |
| 8,980,865 B2 | 3/2015 | Wang | |
| 9,090,642 B2 | 7/2015 | Cho et al. | |
| 9,243,022 B2 | 1/2016 | Beigelman et al. | |
| 9,249,174 B2 | 2/2016 | Beigelman et al. | |
| 9,278,990 B2 | 3/2016 | Smith et al. | |
| 9,388,208 B2 | 7/2016 | Clarke et al. | |
| 9,393,256 B2 | 7/2016 | Ray et al. | |
| 9,481,703 B2 | 11/2016 | Kalayanov et al. | |
| 9,487,544 B2 | 11/2016 | Cho et al. | |
| 9,504,701 B2 | 11/2016 | Casola et al. | |
| 9,540,411 B2 | 1/2017 | Kalayanov et al. | |
| 9,542,154 B2 | 1/2017 | Rubanovich et al. | |
| 9,549,941 B2 | 1/2017 | Cleary et al. | |
| 9,605,018 B2 | 3/2017 | Wang et al. | |
| 9,616,076 B2 | 4/2017 | Casola et al. | |
| 9,701,682 B2 | 7/2017 | Clarke et al. | |
| 9,724,360 B2 | 8/2017 | Chun et al. | |
| 9,828,408 B2 | 11/2017 | Kalayanov | |
| 9,949,994 B2 | 4/2018 | Chun et al. | |
| 10,023,600 B2 | 7/2018 | Butler et al. | |
| 10,034,893 B2 | 7/2018 | Luly et al. | |
| 10,059,716 B2 | 8/2018 | Clarke et al. | |
| 10,065,958 B2 | 9/2018 | Mackman et al. | |

(Continued)

FOREIGN PATENT DOCUMENTS

| | | | |
|---|---|---|---|
| AU | 2010295392 B2 | 4/2012 | |
| CA | 2367921 C | 7/2009 | |

(Continued)

OTHER PUBLICATIONS

Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.

(Continued)

*Primary Examiner* — Jonathan S Lau
(74) *Attorney, Agent, or Firm* — Mintz, Levin, Cohn, Ferris, Glovsky and Popeo, P.C.

(57) ABSTRACT

The present disclosure provides a composition comprising Compound 1, or a pharmaceutically acceptable salt thereof, cyclodextrin, and, optionally, pH adjusting agents.

12 Claims, 2 Drawing Sheets

(56) References Cited

U.S. PATENT DOCUMENTS

| | | |
|---|---|---|
| 10,251,898 B2 | 4/2019 | Chun et al. |
| 10,251,904 B2 | 4/2019 | Clarke et al. |
| 10,377,761 B2 | 8/2019 | Clarke et al. |
| 2003/0050229 A1 | 3/2003 | Sommadossi et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0203015 A1 | 8/2010 | Butler et al. |
| 2010/0234584 A1 | 9/2010 | Chang |
| 2010/0291031 A2 | 11/2010 | Francom et al. |
| 2010/0298257 A1 | 11/2010 | Ross et al. |
| 2010/0305202 A1* | 12/2010 | Hwang .................... A61K 9/19 514/449 |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2016/0058779 A1 | 3/2016 | Casola et al. |
| 2016/0122374 A1* | 5/2016 | Chun .................... C07D 487/04 424/133.1 |
| 2017/0071964 A1 | 3/2017 | Clarke et al. |

FOREIGN PATENT DOCUMENTS

| | | | |
|---|---|---|---|
| CN | 1291994 A | | 4/2001 |
| CN | 1443189 A | | 9/2003 |
| CN | 1498221 A | | 5/2004 |
| CN | 1852915 A | | 10/2006 |
| CN | 101043893 A | | 9/2007 |
| CN | 101611046 A | | 12/2009 |
| CN | 102906102 A | | 1/2013 |
| EA | 201071170 A1 | | 8/2011 |
| EA | 201171417 A1 | | 5/2012 |
| EA | 201200525 A1 | | 9/2012 |
| EP | 2480559 B1 | | 8/2012 |
| EP | 2396340 B1 | | 12/2013 |
| JP | 41017629 | | 10/1966 |
| JP | 2004520367 A | | 7/2004 |
| JP | 2008502685 A | | 1/2008 |
| JP | 2008518934 A | | 6/2008 |
| TW | 1401084 B | | 7/2013 |
| WO | WO-1991/019721 A1 | | 12/1991 |
| WO | WO-1999045029 | | 9/1999 |
| WO | WO-2000/56734 A1 | | 9/2000 |
| WO | WO-2001/32153 A2 | | 5/2001 |
| WO | WO-2001/60315 A2 | | 8/2001 |
| WO | WO-2001/90121 A2 | | 11/2001 |
| WO | WO-2002/008241 | | 1/2002 |
| WO | WO-2002/18404 A2 | | 3/2002 |
| WO | WO-2002/32920 A2 | | 4/2002 |
| WO | WO-2002/057287 A2 | | 7/2002 |
| WO | WO-2002/057425 A2 | | 7/2002 |
| WO | WO-2003/093272 A1 | | 11/2003 |
| WO | WO-2003/093273 A1 | | 11/2003 |
| WO | WO-2003/100009 A2 | | 12/2003 |
| WO | WO-2004/046331 A2 | | 6/2004 |
| WO | WO-2005/009418 A2 | | 2/2005 |
| WO | WO-2005/123087 A2 | | 12/2005 |
| WO | WO-2006/031725 A2 | | 3/2006 |
| WO | WO-2006/050161 A2 | | 5/2006 |
| WO | WO-2006/064033 A2 | | 6/2006 |
| WO | WO-2006/065335 A2 | | 6/2006 |
| WO | WO-2006/121820 A1 | | 11/2006 |
| WO | WO-2007/027248 A2 | | 3/2007 |
| WO | WO-2007/056170 A2 | | 5/2007 |
| WO | WO-2007/064883 A2 | | 6/2007 |
| WO | WO-2007/064931 A2 | | 6/2007 |
| WO | WO-2007/065289 A2 | | 6/2007 |
| WO | WO-2007/065829 A1 | | 6/2007 |
| WO | WO-2007/097991 A2 | | 8/2007 |
| WO | WO-2007/135134 A1 | | 11/2007 |
| WO | WO-2008/005542 A2 | | 1/2008 |
| WO | WO-2008/055870 A1 | | 5/2008 |
| WO | WO-2008/079206 A1 | | 7/2008 |
| WO | WO-2008/082601 A2 | | 7/2008 |
| WO | WO-2008/085508 A2 | | 7/2008 |
| WO | WO-2008/089105 A2 | | 7/2008 |
| WO | WO-2008/116064 A2 | | 9/2008 |
| WO | WO-2008/121634 A2 | | 10/2008 |
| WO | WO-2008/141079 A1 | | 11/2008 |
| WO | WO-2009/009951 A1 | | 1/2009 |
| WO | WO-2009/131926 A1 | | 10/2009 |
| WO | WO-2009/132123 A1 | | 10/2009 |
| WO | WO-2009/132135 A1 | | 10/2009 |
| WO | WO-2010/002877 A2 | | 1/2010 |
| WO | WO-2010/036407 A2 | | 4/2010 |
| WO | WO-2010/093608 A1 | | 8/2010 |
| WO | WO-2010/099458 A1 | | 9/2010 |
| WO | WO-2010/135569 A1 | | 11/2010 |
| WO | WO-2011/011303 A1 | | 1/2011 |
| WO | WO-2010/111381 A3 | | 3/2011 |
| WO | WO-2011/035231 A1 | | 3/2011 |
| WO | WO-2011/035250 A1 | | 3/2011 |
| WO | WO-2011080568 | | 7/2011 |
| WO | WO-2011/123645 A2 | | 10/2011 |
| WO | WO-2011/123672 A1 | | 10/2011 |
| WO | WO-2011123668 | | 10/2011 |
| WO | WO-2011/150288 A1 | | 12/2011 |
| WO | WO-2012/012465 A1 | | 1/2012 |
| WO | WO-2012/012776 A1 | | 1/2012 |
| WO | WO-2012/039787 A1 | | 3/2012 |
| WO | WO-2012/039791 A1 | | 3/2012 |
| WO | WO-2012/051570 A1 | | 4/2012 |
| WO | WO-2012142523 | | 10/2012 |
| WO | WO-2013/084165 A1 | | 6/2013 |
| WO | WO-2014/042433 A2 | | 3/2014 |
| WO | WO-2014033617 | | 3/2014 |
| WO | WO-2014/078778 A2 | | 5/2014 |
| WO | WO-2014078463 | | 5/2014 |
| WO | WO-2014/116755 A1 | | 7/2014 |
| WO | WO-2014169280 | | 10/2014 |
| WO | WO-2015/069939 A1 | | 5/2015 |
| WO | WO-2016/069825 A1 | | 5/2016 |
| WO | WO-2016/069826 A1 | | 5/2016 |
| WO | WO-2016/069827 A1 | | 5/2016 |

(56) References Cited

FOREIGN PATENT DOCUMENTS

WO    WO-2017/184668 A1    10/2017
WO    WO-2017/049060 A1    3/2018

OTHER PUBLICATIONS

Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.
Arimilli, M.N., et al., Synthesis, in Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.
ARIPO Form 21 and Substantive Examination Report (in English) for AP Application No. AP/P/2010/005439, dated Mar. 18, 2014.
ARIPO Patent Office, Official Action (ARIPO Form No. 18) with Substantive Search and Examination Report for AP Application No. AP/P/2010/005414, dated Mar. 14, 2014.
ARIPO Patent Office, Search and Exam Report for AP Application No. AP/P/2012/006189, dated Jun. 26, 2014.
ARIPO Patent Office, Search Report for AP Patent Application No. AP/P/2011/005818, dated Sep. 19, 2013.
Asbun, et al., Synthesis of 5-substituted Pyrimidines. II, Journal of Organic Chemistry, 1968, pp. 140-142, vol. 31.
Australia Patent Office, Patent Examination Report No. 1 for AU Application No. 2011280910, dated Jun. 10, 2014.
Australia Patent Office, Patent Examination Report No. 1 for AU Application No. 2011306066, dated Nov. 21, 2013.
Australia Patent Office, Patent Examination Report No. 1 for AU Patent Application No. 2010213873, dated Jun. 4, 2014.
Australia Patent Office, Patent Examination Report No. 1 for AU Patent Application No. 2010295392, dated Sep. 16, 2014.
Australia Patent Office, Patent Examination Report No. 1 for AU Patent Application No. 2011282241, dated Jul. 9, 2014.
Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.
Balzarini, et al., Inhibition of feline (FIPV) and human (SARS) coronavirus by semisynthetic derivatives of glycopeptide antibiotics, Antiviral Research, Mar. 14, 2006, pp. 20-33, vol. 72.
Bandini, et al., Indium tribromide: a highly effective catalyst for the addition of trimethylsilyl cyanide to α-hetero-substituted ketone, Tetrahedron Letters, 2001, pp. 3041-3043. vol. 42.
Barker, et al., 2,3,5-Tri-O-benzyl-D-ribosyl and -L-arabinosyl Bromides, Journal of Organic Chemistry, 1961, pp. 4605-4609, vol. 26, No. 11.
Belokon, et al., Optimized catalysts for the asymmetric addition of trimethylsilyl cyanide to aldehydes and ketones, Tetrahedron, 2001, pp. 771-779, vol. 57.
Benksim, et al., A Novel Stereospecific Synthesis of Glycosyl Cyanides from 1,2-O-sulfinyl Derivatives, Organic Letters, 2004, pp. 3913-3915, vol. 6, No. 22.
Benzaria, et al., Synthesis, in Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability, J. Med. Chem., 1996, pp. 4958-4965, vol. 39, No. 25.
Bio, et al., Practical Synthesis of a Potent Hepatitis C Virus RNA Replication Inhibitor, J. Org. Chem., 2004, pp. 6257-6266, vol. 69, No. 19.
Bobeck, et al., Advances in Nucleoside Monophosphate Prodrugs as Anti-HCV Agents, Antiviral Therapy, 2010, pp. 935-950, vol. 15.
Bojack, et al., Design and Synthesis of Inhibitors of Adenosine and AMP Deaminases, Org. Letters, 2001, pp. 839-842, vol. 3, No. 6.
Boyer, et al., Pathogenesis, diagnosis and management of hepatitis C, Journal of Hepatology, 2000, pp. 98-112, vol. 32.

Brown, Progress towards improving antiviral therapy for hepatitis C virus polymerase inhibitors. Part O: Nucleoside analogues, 2009, pp. 709-725, vol. 18.
Burns, A glimmer of hope for a fatal feline disease, American Veterinary Medical Association, Dec. 15, 2017, 5 pages.
Butora, et al., Synthesis and HCV inhibitory properties of 9-deaza- and 7,9-dideaza-7-oxa-2'-C-methyladenosine, Bioorganic & Medicinal Chemistry, 2007, pp. 5219-5229, vol. 15, No. 15.
Cabirol, et al., Robust and Efficient, yet Uncatalyzed, Synthesis of Triarylsilyl-protected Cyanohydrins from Ketones, 2008, pp. 2446-2449, vol. 73.
Calès, et al., Treatment of liver fibrosis: clinical aspects, Gastroentérologie Clinique et Biologique, 2009, pp. 958-966, vol. 33, No. 10-11.
Calisher, et al., Antigenic Relationships between Flaviviruses as Determined by Cross-neutralization Tests with Polyclonal Antisera, Journal of General Virology, 1989, pp. 37-43, vol. 70.
Camps, Studies on Structurally Simple-αβ-butenolides-II, Tetrahedron, 1982, pp. 2395-2402, vol. 38, No. 15.
Canadian Patent Office, Office Action for CA Patent Application No. 2,773,772, dated Aug. 12, 2014.
Carroll, Robust Antiviral Efficacy upon Administration of a Nucleoside Analog to Hepatitis C Virus-Infected Chimpanzees, Antimicrobial Agents and Chemotherapy, 2009, pp. 926-934, vol. 53, No. 3.
Chapman, et al., RSV604, a Novel Inhibitor of Respiratory Syncytial Virus Replication, Antimicrobial Agents and Chemotherapy, 2007, pp. 3346-3353, vol. 51, No. 9.
Chile Patent Office, Opposition filed Against CL Patent Applicatioh 00076-2013, dated Jun. 18, 2014.
Chile Patent Office, Opposition for CL Patent Application No. 727-2013, dated Oct. 15, 2013.
Chile Patent Office, Second Office Action for CL Patent Application No. 1906-2011, dated Oct. 16, 2013.
Chinese Patent Office, Office Action for CN Patent Application No. 200980114224.2, dated Nov. 30, 2012.
Chinese Patent Office, Notification of Reexamination for CN Patent Application No. 200980120218.8, dated Sep. 1, 2014.
Chinese Patent Office, Notification of the First Office Action and Search Report for CN Patent Application No. 201080041902.X, dated Nov. 12, 2013.
Chinese Patent Office, Notification of the First Office Action for CN Patent Application No. 201180035776.1, dated Feb. 27, 2014.
Chinese Patent Office, Notification of the First Office Action, with Search Report, for CN Patent Application No. 201080041946.2, dated Dec. 18, 2013.
Chinese Patent Office, Notification of the Second Office Action & Search Report for CN Patent Application No. 201080011690.0, dated Jan. 8, 2014.
Chinese Patent Office, Notification of the Third Office Action for CN Patent Application No. 201080011690.0, dated Jul. 29, 2014.
Chinese Patent Office, Office Action for CN Patent Application No. 200980114224.2, dated Aug. 19, 2013.
Chinese Patent Office, Office Action with Search Report for CN Patent Application No. 201180035281.9, dated Jun. 27, 2014.
Chinese Patent Office, Rejection Decision for CN Patent Application No. 200980120218.8, dated Feb. 7, 2014.
Chinese Patent Office, Second Examination Report for CN Patent Application No. 200980120218.8, dated Jun. 21, 2013.
Cho, et al., Synthesis and antiviral activity of a series of 1'-substituted 4-aza-7,9-dideazaadenosine C-nucleosides, Bioorg. Med Chem. Letters, 2012, pp. 2705-2707, vol. 22.
Cihlar, et al., Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131, Antimicrobial Agents and Chemotherapy, 2008, pp. 655-665, vol. 52, No. 2.
Clark, et al., Design, Synthesis, and Antiviral Activity of 2'-Deoxy-2'-fluoro-2'-C-methylcytidine, a Potent Inhibitor of Hepatitis C Virus Replication, Journal of Medicinal Chemistry, 2005, pp. 5504-5508, vol. 48, No. 17.
Clarke, et al., Discovery of [beta]-d-2'-deoxy-2'-[alpha]-fluoro-4'[alpha]-cyano-5-aza-7,9-dideaza adenosine as a potent nucleoside inhibitor of respiratory syncytial virus with excellent selectivity over mitochondrial, BioOrganic & Medicinal Chemistry Letters, Apr. 29, 2015, pp. 2484-2487, vol. 25, No. 12.

(56) References Cited

OTHER PUBLICATIONS

Colacino, et al., Synthesis and Biological Evaluation of Some 5-Nitro- and 5-Amino Derivatives of 2'-Deoxycytidine, 2',3'-Dideoxyuridine, and 2',3'-Dideoxycytidine, Nucleoside, Nucleotides & Nucleic Acids, 2003, pp. 2013-2026, vol. 22, No. 11.
Columbia Patent Office, Office Action for CO Application No. 13 004212, dated Dec. 4, 2013.
Columbia Patent Office, Office Action for CO Patent Application No. 11-109.501, dated Nov. 27, 2012.
Columbia Patent Office, Office Action for CO Patent Application No. 13-235103-1, dated Aug. 27, 2014.
Columbia Patent Office, Resolution No. 56673 for CO Patent Application No. 10-31479, dated Sep. 27, 2013.
Columbia Patent Office, Resolution No. 72986 for CO Patent Application No. 10-121513-5, dated Dec. 23, 2013.
Columbia Patent Office, Second Examination Report (in English) for CO Patent Application No. 10-131479, dated Jun. 20, 2013.
Columbian Patent Office, Office Action No. 425 for CO Patent Application No. 12 050 579, dated Jan. 21, 2014.
Communication pursuant to Article 94(3) EPC for EP Patent Application No. 10763083.2, dated May 2, 2014.
Communication pursuant to Article 94(3) EPC for EP Patent Application No. 11715792.5, dated Feb. 14, 2014.
Communication under 161/162 for EP Patent Application No. 10704068.5, dated Sep. 6, 2011.
Communication under 161/162 for EP Patent Application No. 10763083.2, dated May 11, 2012.
De Clercq, Molecular Targets for Antiviral Agents, the Journal of Pharmacology and Experimental Therapeutics, 2001, pp. 1-10, vol. 297, No. 1.
De Francesco, et al., Approaching a New Era for Hepatitis C Virus Therapy: Inhibitors of the NS3-4A Serine Protease and the NS5B RNA-Dependent RNA Polymerase, Antiviral Research, 2003, pp. 1-16, vol. 58, No. 1.
De Las Heras, Synthesis of Ribosyl and Arabinosyl Cyanides by Reaction of 1-O-Acyl Sugars with Trimethylsilyl Cyanide, Journal of the Chemical Society, Perkin Transactions 1, 1982, pp. 903-907.
De Lombaert, et al., N-Phosphonomethyl Dipeptides and Their Phosphonate Prodrugs, a New Generation of Neutral Endopeptidase (NEP, EC 3.4.24.11) Inhibitors, J. Med. Chem., 1994, pp. 498-511, vol. 37, No. 4.
Di Bisceglie, et al., The Unmet Challenges of Hepatitis C, Scientific American, Oct. 1999, pp. 80-85.
Dolzhenko, et al., Pyrazolo[1,5-a][1,3,5]Triazines(5-Aza-9-Deazapurines): Synthesis and Biological Activity, Heterocycles, 2008, pp. 1575-1622, vol. 75, No. 7.
Domingo, et al., The quasispecies (extremely heterogeneous) nature of viral RNA genome populations: biological relevance—a review, Gene, 1985, pp. 1-8, vol. 40.
Dondoni, et al., Thiazole-Based Synthesis of Formyl C-Glycosides, Journal of Organic Chemistry, 1994, pp. 6404-6414, vol. 59.
Dudfield, et al., Synthesis of C-ribosyl 1,2,4-triazolo[3,4-f][1,2,4]triazines as Inhibitors of Adenosine and AMP Deaminasses, J. Chem. Soc., Perkin Trans. 1, 1999, pp. 2937-2942.
Dudfield, et al., Synthesis of C-ribosyl Imidazo[2,1-f][1,2,4]triazines as Inhibitors of Adenosine and AMP Deaminases, J. Chem. Soc., Perkin Trans. 1, 1999, pp. 2929-2936.
Dymock, et al., Novel approaches to the treatment of hepatitis C virus infection, Antiviral Chemistry & Chemotherapy, 2000, pp. 79-96, vol. 11, No. 2.
Ecuador Patent Office, Opposition for EC Patent Application No. SP-13-12451, dated Apr. 23, 2014.
Ecuador Patent Office, Opposition for EC Patent Application No. SP-2012-11817, dated May 27, 2013.
Ecuador Patent Office, Statement of Opposition for EC Patent Application No. SP-10-10609, dated Mar. 31, 2011.
El Safadi, et al., 5-Modified-2'-dU and 2'-dC as Mutagenic Anti HIV-1 Proliferation Agents: Synthesis and Activity, Journal of Medicinal Chemistry, 2010, pp. 1534-1545, vol. 53, No. 4.

El Salvador Patent Office, Official Action for SV National Phase Entry of International Application No. PCT/US2010/049471, dated Nov. 6, 2013.
English translation of Office Action for MX Application No. MX/a/2013/003179, dated Feb. 25, 2014.
Eurasian Patent Office, Office Action for EA Patent Application No. 201390152, dated Apr. 14, 2014.
Eurasian Patent Office, Official Action for EA Patent Application No. 201390133, dated Mar. 27, 2014.
Eurasian Patent Office, Second Examination Report for EA Patent Application No. 201071128, dated Oct. 24, 2012.
Eurasian Patent Office, Second Examination Report for EA Patent Application No. 201071170, dated Oct. 25, 2012.
Eurasian Patent Office, Third Examination Report for EA Patent Application No. 201071128, dated Apr. 29, 2013.
Eurasian Patent Office, Third Examination Report for EA Patent Application No. 201071170, dated Oct. 10, 2013.
Eurasian Patent Office, Third Office Action for EA Application No. 201190110/28, dated Oct. 18, 2013.
European Patent Office, International Preliminary Report on Patentability and Written Opinion for PCT International Application No. PCT/US2009/041432, dated Oct. 26, 2010, 7 pages.
European Patent Office, International Preliminary Report on Patentability and Written Opinion for PCT International Application No. PCT/US2010/049471, dated Mar. 27, 2012, 7 pages.
European Patent Office, International Preliminary Report on Patentability and Written Opinion for PCT International Application No. PCT/US2010/049508, dated Mar. 27, 2012, 6 pages.
European Patent Office, International Preliminary Report on Patentability and Written Opinion for PCT International Application No. PCT/US2011/038253, dated Dec. 4, 2012, 6 pages.
European Patent Office, International Preliminary Report on Patentability and Written Opinion for PCT International Application No. PCT/US2011/044581, dated Jan. 22, 2013, 7 pages.
European Patent Office, International Preliminary Report on Patentability for PCT International Application No. PCT/US2009/041447, dated Oct. 26, 2010, 7 pages.
European Patent Office, International Preliminary Report on Patentability for PCT International Application No. PCT/US2010/023586, dated Aug. 16, 2011, 6 pages.
European Patent Office, International Preliminary Report on Patentability for PCT International Application No. PCT/US2011/028897, dated Mar. 26, 2013, 7 pages.
European Patent Office, International Preliminary Report on Patentability for PCT International Application No. PCT/US2011/029441, dated Mar. 26, 2013, 7 pages.
European Patent Office, International Preliminary Report on Patentability for PCT International Application No. PCT/US2011/045102, dated Jan. 22, 2013, 5 pages.
European Patent Office, International Preliminary Report on Patentability for PCT International Application No. PCT/US2015/057932, dated May 2, 2017, 11 pages.
European Patent Office, International Preliminary Report on Patentability for PCT International Application No. PCT/US2015/057933, dated May 2, 2017, 7 pages.
European Patent Office, International Preliminary Report on Patentability for PCT International Application No. PCT/US2015/057934, dated May 2, 2017, 14 pages.
European Patent Office, International Preliminary Report on Patentability for PCT International Application No. PCT/US2015/057934, dated May 11, 2017, 14 pages.
European Patent Office, International Search Report for PCT International Application No. PCT/US2011/038253, dated Jul. 29, 2011, 4 pages.
European Patent Office, International Search Report for PCT International Application No. PCT/US2011/044581, dated Nov. 7, 2011, 4 pages.
European Patent Office, International Search Report for PCT International Application No. PCT/US2009/041432, dated Aug. 11, 2009, 5 pages.
European Patent Office, International Search Report issued in International Application No. PCT/US2010/049471, dated Nov. 18, 2010, 5 pages.

(56) References Cited

OTHER PUBLICATIONS

European Patent Office, International Search Report issued in International Application No. PCT/US2010/049508, dated Nov. 5, 2010, 4 pages.
European Patent Office, International Search Report issued in International Application No. PCT/US2011/028897, dated Aug. 1, 2011, 6 pages.
European Patent Office, International Search Report issued in International Application No. PCT/US2011/029441, dated Aug. 1, 2011, 5 pages.
European Patent Office, International Search Report issued in International Application No. PCT/US2011/045102, dated Nov. 9, 2011, 4 pages.
European Patent Office, International Search Report issued in International Application No. PCT/US2009/041447, dated Aug. 7, 2009, 5 pages.
European Patent Office, Written Opinion and ISR for International Application No. PCT/US2015/057933, dated Jan. 21, 2016, 9 pages.
European Patent Office, Written Opinion and ISR for PCT International Application No. PCT/ US2015/057934, dated May 6, 2016, 20 pages.
European Patent Office, Written Opinion and ISR for PCT International Application No. PCT/US2015/057932, dated May 6, 2016, 7 pages.
European Patent Office, Written Opinion for PCT International Application No. PCT/US2010/023586, dated Aug. 4, 2010, 5 pages.
European Patent Office, Written Opinion for PCT International Application No. PCT/US2011/028897, dated Aug. 1, 2011, 6 pages.
European Patent Office, Written Opinion for PCT International Application No. PCT/US2011/029441, dated Aug. 1, 2011, 6 pages.
European Patent Office, Written Opinion for PCT International Application No. PCT/US2011/038253, dated Jul. 29, 2011, 5 pages.
European Patent Office, Written Opinion for PCT International Application No. PCT/US2011/044581, dated Nov. 7, 2011, 6 pages.
European Patent Office, Written Opinion for PCT International Application No. PCT/US2011/045102, dated Nov. 9, 2011, 4 pages.
European Patent Office, Written Opinion issued in International Application No. PCT/US2009/041447, dated Oct. 26, 2010, 7 pages.
European Patent Office, Written Opinion issued in International Application No. PCT/US2010/049471, dated Mar. 27, 2012, 7 pages.
European Patent Office, Written Opinion issued in International Application No. PCT/US2010/049508, dated Mar. 27, 2012, 6 pages.
European Patent Office, International Search Report for PCT International Application No. PCT/US2016/052092, dated Oct. 11, 2016, 11 pages.
European Patent Office, Written Opinion issued in International Application No. PCT/US2011/045102, dated Jan. 22, 2013, 5 pages.
European Patent Office, Written Opinion issued in International Application No. PCT/US2017/028243, dated Aug. 29, 2017, 12 pages.
European Patent Office, International Search Report for PCT International Application No. PCT/US2018/0022166, dated Jun. 11, 2018, 18 pages.
European Patent Office, International Search Report for PCT International Application No. PCT/US2018/022166, dated Jun. 11, 2018, 18 pages.
Extended European Search Report for EP Application No. 13194605.5, dated Mar. 13, 2014.
Farquhar, et al., Biologically Reversible Phosphate-Protective Groups, Journal of Pharmaceutical Sciences, 1983, pp. 324-325, vol. 72, No. 3.
First Examination Report (in English) for CO Patent Application No. 10-131479, dated Oct. 23, 2012.
First Examination Report (in English) for MX Patent Application No. MX/a/2010/011661, dated Oct. 26, 2011.
First Examination Report for AU Patent Application No. 2009240630, dated Jun. 14, 2012.
First Examination Report for AU Patent Application No. 2009240642, dated Aug. 2, 2012.
First Examination Report for CN Patent Application No. 200980120218.8, dated Nov. 13, 2012.
First Examination Report for CO Patent Application No. 10-121513-5, dated Dec. 10, 2012.
First Examination Report for EA Patent Application No. 201071128, dated Apr. 25, 2012.
First Examination Report for EA Patent Application No. 201071170, dated Apr. 25, 2012.
First Examination Report for ID Patent Application No. WO 2010 03923, dated Apr. 5, 2013.
First Examination Report for ID Patent Application No. WO 2010 03957, dated Apr. 25, 2013.
First Examination Report for IL Patent Application No. 208515, dated Jan. 6, 2013.
First Examination Report for IL Patent Application No. 208701, dated Jan. 13, 2013.
First Examination Report for JP Patent Application No. 2011-506429, dated Aug. 22, 2013.
First Examination Report for JP Patent Application No. 2011-506435, dated Aug. 22, 2013.
First Examination Report for NZ Patent Application No. 588400, dated Apr. 11, 2011.
First Examination Report for NZ Patent Application No. 588670, dated Apr. 8, 2011.
First Examination Report for NZ Patent Application No. 608070, dated Nov. 7, 2013.
First Examination Report for TW Patent Application No. 098113324, dated Oct. 30, 2012.
First Examination Report for UA Patent Application No. 2010 13030, dated Mar. 2, 2013.
First Examination Report for VN Patent Application No. 1-2010-02653, dated Apr. 26, 2012.
First Examination Report for VN Patent Application No. 1-2010-02939, dated Apr. 19, 2012.
First Office Action for CL Patent Application No. 1906-2011, dated May 7, 2013.
First Office Action for CN Patent Application No. 201080011960.0, dated Jun. 8, 2013.
First Office Action for EA Patent Application No. 201190110/28, dated Apr. 26, 2012.
First Office Action for EA Patent Application No. 201390141/28, with English translation, dated Aug. 14, 2014.
First Office Action for EP Patent Application No. 10704068.5, dated Jun. 18, 2012.
First Office Action for IL Patent Application No. 214396, dated Jul. 8, 2013.
First Office Action for UA Application No. a 2011 10568, dated Apr. 7, 2014.
First Office Action for VN Patent Application No. 1-2012-03895, dated Feb. 8, 2013.
Form 21 for AP Patent Application No. AP/P/2011/005818, dated Sep. 19, 2013.
Fukumoto, et al., Viral Dynamics of Hepatiis C Early After Orthotopic Liver Transplantation: Evidence for Rapid Turnover of Serum Virions, Hepatology, 1996, pp. 1351-1354, vol. 24.
Further Examination Report for NZ Application No. 594370, dated Oct. 8, 2013.
Garcia, et al., Synthesis of (2,3,4,6-tetra-O-acetyl-alpha-D-glycopyranosyl)thiophene derivatives as new C-nucleoside analogues, J. Carbohydrate Chemistry, 2001, pp. 681-687, vol. 20, No. 7/8.
Gardelli, et al., Phosphoramidate Prodrugs of 2'-C-Methylcytidine for Therapy of Hepatitis C Virus Infection, Journal of Medicinal Chemistry, 2009, pp. 5394-5407, vol. 52, No. 17.
Gleeson, et al., Prediction of the Potency of Inhibitors of Adenosine Deaminase by QM/MM Calculations, Chem. Commun., 2003, pp. 2180-2181.
Gordon, et al., Control of Hepatitis C: A Medicinal Chemistry Perspective, J. Med. Chem., 2005, pp. 1-20, vol. 48, No. 1.
Greene, Protective Groups in Organic Synthesis, 1991, 15 pages, John Wiley & Sons, New York.

(56) References Cited

OTHER PUBLICATIONS

Gudmundsson, et al., Synthesis of imidazo[1,2-a]pyridine C-Nucleosides with an Unexpected Site of Ribosylation, Journal of Organic Chemistry, 1997, pp. 3453-3459, vol. 62.

Gudmundsson, et al., The Condensation of 2,6-dichloroimidazo[1,2-a]pyridine C-nucleoside with an Unexpected Site of Ribosylation, Tetrahedron Letters, 1996, pp. 2365-2368, vol. 7, No. 14.

Gunic, et al., Cyclic monophosphate prodrugs of base-modified 2'-C-methyl ribonucleosides as potent inhibitors of hepatitis C virus RNA replication, Bioorganic & Medicinal Chemistry Letters, 2007, pp. 2452-2455, vol. 17.

Hamann, et al., Synthesis and antiviral evaluation of 7,9-dideaza-8-thiapurine C-nucleoside derivatives, Collection Symposium Series, 2008, pp. 347-349, vol. 10.

Hamann, et al., Synthesis and antiviral evaluation of thieno[3,4-d]pyrimidine C-nucleoside analogues of 2',3'-dideoxy- and 2',3'-dideoxy-2',3'-didehydro-adenosine and -inosine, Bioorganic & Medicinal Chemistry, 2009, pp. 2321-2326, vol. 17.

Han, et al., Synthesis of 1-Chloroacetyl-1-dehydroxy-2,3,5-tri-O-benzoyl-β-D-ribofuranose. A Potentially Versatile Intermediate for the Synthesis of C-Nucleosides, Synthetic Communications, 1992, pp. 2815-2822, vol. 22, No. 19.

Haraguchi, et al., Stereoselective Synthesis of 1'-C-Branched Uracil Nucleosides From Uridine, Nucleosides & Nucleotides, 1995, pp. 417-420, vol. 14, No. 3-5.

Harki, et al., Synthesis and Antiviral Activity of 5-Substituted Cytidine Analogues: Identification of Potent Inhibitor of Viral RNA-Dependent RNA Polymerases, Journal of Medicinal Chemistry, 2006, pp. 6166-6169, vol. 49, No. 21.

Hayashi, et al., C-Nucleosides. 17. A Synthesis of 2-Substituted 7-(B-D-Ribofuranosyl)-Pyrrolo[2,1-f]-1,2,4-Triazines. A New Type of "Purine Like" C-Nucleoside, Heterocycles, 1992, pp. 569-574, vol. 34, No. 3.

Hecker, et al., Liver Targeted Prodrugs of 2'-C-Methyladenosine for Therapy of Hepatitis C Virus Infection, J. Med. Chem., 2007, pp. 3891-3896, vol. 50, No. 16.

Hoffman, et al., When, in the Context of Drug Design, Can a Fluorine Atom Successfully Substitute a Hydroxyl Group?, International Journal of Quantum Chemistry, 2002, pp. 419-427, vol. 89.

Indonesia Patent Office, Substantive Examination Report Stage 1 for ID Application No. W-00201103126, dated Jun. 10, 2014.

Israel Patent Office, Notification of Defects for IL Patent Application No. 208515, dated Aug. 25, 2014.

Israel Patent Office, Notification of Defects for IL Patent Application No. 214396, dated Nov. 11, 2013.

Israel Patent Office, Notification of Defects for IL Patent Application No. 218599, dated Aug. 25, 2014.

Israel Patent Office, Notification of Defects for IL Patent Applicaton No. 208701, dated Aug. 25, 2014.

Israel Patent Office, Notification Prior to Examination for IL Patent Application No. 218599, dated Nov. 13, 2012.

Israel Patent Office, Notification Prior to Examination for IL Patent Application No. 218752, dated Jan. 20, 2014.

Israel Patent Office, Supplement to First Examination Report for IL Patent Application No. 208515, dated Jan. 15, 2013.

Itoh, et al., Divergent and Stereocontrolled Approach to the Synthesis of Uracil Nucleosides Branched at the Anomeric Position, J. Org. Chem., 1995, pp. 656-662, vol. 60, No. 3.

Japanese Patent Office, Notice of Reasons for Rejection for JP Application No. 2011-549324, dated Jul. 28, 2014.

Japanese Patent Office, Notice of Reasons for Rejection for JP Application No. 2011-549324, dated Mar. 26, 2014.

Japanese Patent Office, Notification of Reasons for Rejection for JP Patent Application No. 2012-529958, dated Aug. 5, 2014.

Japanese Patent Office, Notification of Reasons for Rejection for JP Patent Application No. 2012-529963, dated Aug. 28, 2014.

Jasko, et al., 5'-Phosphonates of Ribonucleosides and 2'-Deoxyribonucleosides: Synthesis and Antiviral Activity, Nucleosides & Nucleotides, 1993, pp. 879-893, vol. 12, No. 8.

Kabat, et al., Nucleosides, CXLVIII, Synthesis of 6-(β-D-Ribofuranosyl)picolinamide: A Novel C-Nucleoside from D-Ribonolactone, Chemical & Pharmaceutical Bulletin, 1988, pp. 634-640, vol. 36, No. 2.

Kim, et al., Reversal of the Progression of Fatal Coronavirus Infection in Cats by a Broad-Spectrum Coronavirus Protease Inhibitor, PLOS Pathogens, Mar. 30, 2016, p. e1005531, vol. 12, No. 3.

Khamnei, et al., Neighboring Group Catalysis in the Design of Nucleotide Prodrugs, J. Med. Chem., 1996, pp. 4109-4115, vol. 39, No. 20.

Klumpp, et al., The Novel Nucleoside Analog R1479 (4'-Azidocytidine) is a Potent Inhibitor of NSSB-dependent RNA Synthesis and Hepatitis C virus Replication in Cell Culture, Journal of Biological Chemistry, 2006, pp. 3793-3799, vol. 281, No. 7.

Knutsen, et al., Synthesis of Imidazo-fused Bridgehead-nitrogen 2'-Deoxyribo-C-nucleosides: Coupling-Elimination Reactions of 2,5-Anhydro-3,4,6-tri-O-benzoyl-o-allonic Acid, J. Chem. Soc., Perkin Trans. 1, 1985, pp. 621-630.

Knutsen, et al., Synthesis of Imidazo-fused Bridgehead-nitrogen C-Nucleosides via Dehydrative Coupling Reactions of 2,5-Anhydro-3,4,6-tri-O-benzoyl-D-allonic Acid, J. Chem. Soc., Perkin Trans 1, 1984, pp. 229-238.

Kobe, et al., Use of Distance Geometry Approach for the in Vitro Antiviral Activity Evaluation of N-bridgehead C-nucleosides, European J. Med. Chem., 1992, pp. 259-266, vol. 27, No. 3.

Lefebvre, et al., Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate, Journal of Medicinal Chemistry, 1995, pp. 3941-3950, vol. 38, No. 20.

Lefebvre, et al., Synthesis, Decomposition Pathways and 'in Vitro' Evaluation of Bioreversible Phosphotriesters of Azt, Nucleosides, Nucleotides & Nucleic Acids, 1995, pp. 763-766, vol. 14, No. 3-5.

Lindell, et al., Synthesis and Biochemical Testing of 3-(Carboxyphenylethyl)imidazo[2,1-f][1,2,4]triazines as Inhibitors of AMP Deaminase, ACS Medicinal Chemistry Letters, 2010, pp. 286-289, vol. 1, No. 6.

Lovelette, 1,2,4-Triazines. Synthesis of selected members of the s-triazolo[3,4-f][1,2,4]triazine and tetrazolo[1,5-f][1,2,4]triazine ring systems, Journal of Heterocyclic Chemistry, 1979, pp. 555-560, vol. 16.

Martell, et al., Hepatitis C Virus (HCV) Circulates as a Population of Different but Closely Related Genomes: Quasispecies Nature of HCV Genome Distribution, Journal of Virology, 1992, pp. 3225-3229, vol. 6695.

Mason, et al., Polyadenylation-dependent screening assay for respiratory syncytial virus RNA transcriptase activity and identification of an inhibitor, Nucleic Acids Research, 2004, pp. 4758-4767, vol. 32, No. 16.

Matulic-Adamic, et al., Synthesis of 3-(β-D-Ribofuranosyl)-2-Fluoropyridine and 3-(β-D-Ribofuranosyl)-Pyridin-2-one, Tetrahedron Letters, 1997, pp. 203-206, vol. 38, No. 2.

Matulic-Adamic, et al., Synthesis of 5-(β-D-Ribofuranosyl)-Pyridin-2-one: a 'Deletion-Modified' Analogue of Uridine, Tetrahedron Letters, 1997, pp. 1669-1672, vol. 38, No. 10.

McGuigan, et al., Intracellular Delivery of Bioactive AZT Nucleotides by Aryl Phosphate Derivatives of AZT, J. Med. Chem., 1993, pp. 1048-1052, vol. 36, No. 8.

Meppen, et al., Cyclic phosphoramidates as prodrugs of 2'-C-methylcytidine, European Journal of Medicinal Chemistry, 2009, pp. 3765-3770, vol. 49, No. 9.

Meppen, et al., Medi-404—A Prodrug Approach for the Treatment of HCV Infection, Abstracts of papers, 236th ACS National Meeting, Philadelphia, PA, United States, Aug. 17-21, 2008.

Metobo, et al., Practical synthesis of 10-substituted Tubercidin C-nucleoside analogs, Tetrahedron Letters, 2011, pp. 484-486, vol. 53.

Mexico Patent Office, Office Action for MX Application No. MX/a/2013/000656, dated Apr. 22, 2014.

Mexico Patent Office, Office Action for MX Application No. MX/a/2013/000656, dated Aug. 4, 2014.

Mexico Patent Office, Office Action for MX Application No. MX/a/2013/000744, dated Apr. 22, 2014.

(56) References Cited

OTHER PUBLICATIONS

Migliaccio, et al., Characterization of Resistance to Non-obligate Chain-terminating Ribonucleoside Analogs That Inhibit Hepatitis C Virus Replication in vitro, the Journal of Biological Chemistry, 2003, pp. 49164-49170, vol. 278, No. 49.
Mitchell, et al., Bioreversible Protection for the Phospho Group: Bioactivation of the Di(4-acyloxybenzyl) and Mono(4-acyloxybenzyl) Phosphoesters of Methylphosphonate and Phosphonoacetate, J. Chem. Soc., Perkin Trans. 1, 1992, pp. 2345-2353.
Mitchell, et al., Synthesis of C-Nucleoside Isosteres of 9-(2-Hydroxyethoxymethyl)guanine (Acyclovir), J. Het. Chem., 1984, pp. 697-699, vol. 21, No. 3.
Moennig, et al., The Pestiviruses, Advances in Virus Research, 1992, pp. 53-98, vol. 41.
Moradpour, et al., Replication of hepatitis C virus, Nature Reviews Microbiology, 2007, pp. 453-463, vol. 5, No. 6.
Moscow, et al., Reduced Folate Carrier Gene (RFC1) Expression and Anti-Folate Resistance in Transfected and Non-Selected Cell Lines, International Journal of Cancer, 1997, pp. 184-190, vol. 72.
Murakami, et al., Mechanism of Activation of Beta-D-2'-Fluoro-2'-C-Methylcytidine and Inhibition of Hepatitis C Virus NS5B RNA Polymerase, Antimicrob Agents Chemother., Feb. 2007, pp. 503-509, vol. 51, No. 2.
Murphy, et al., The nucleoside analog GS-441524 strongly inhibits feline infections peritonitis (FIP) virus in tissue culture and experimental cat infection studies, Veterinary Microbiology, ND, pp. 226-233, vol. 219.
Neumann, et al., Hepatitis C Viral Dynamics in Vivo and the Antiviral Efficacy of Interferon—α Therapy, Science, 1998, pp. 103-107, vol. 282.
New Zealand Patent Office, Second Examination Report and Notice of Acceptance for NZ Patent Application No. 588400, dated Jul. 27, 2012.
Nishimura, et al., Synthesis of pyrrolo[2,1-f][1,2,4]triazine C-nucleosides, Isosteres of sangivamycin, tubercidin, and toyocamycin, Carbohydrate Research, 2001, pp. 77-82, vol. 331, No. 1.
Ogura, et al., Reaction of Ethynyl Compounds with Lactones, Journal of Organic Chemistry, 1972, pp. 72-75, vol. 37, No. 1.
Otter, et al., Conformational Properties of Purine-Like C-Nucleosides, Nucleosides & Nucleotides, 1996, pp. 793-807, vol. 15, No. 1-3.
Pankiewicz, et al., C-Nucleoside Analogues of Nicotinamide Mononucleotide (NMN), Nucleosides and Nucleotides, 1988, pp. 589-593, vol. 7, No. 5&6.
Pankiewicz, et al., Efficient Synthesis of 5-(β-D-Ribofuranosyl)nicotinamide and its α-Isomer, Journal of Organic Chemistry, 1988, pp. 3473-3479, vol. 53.
Patil, et al., C-Glycosylation of Substituted Heterocycles under Friedel-Crafts Conditions (II): Robosylation of Multi-Functionalized Thiophenes and Furans for the Synthesis of Purine-Like C-Nucleosides, Nucleosides & Nucleotides, 1990, pp. 937-956, vol. 9, No. 7.
Patil, et al., 4-Aza-7,9-Dideazaadenosine, a New Cytotoxic Synthetic C-Nucleoside Analogue f Adenosine, Tet. Lett., 1994, pp. 5339-5342, vol. 35.
Patil, et al., Synthesis of Pyrrolo[2,1-f][1,2,4]triazine Congeners of Nucleic Acid Purines via the N-Amination of 2-Substituted Pyrroles, J. Het. Chem., 1994, pp. 781-786, vol. 31.
Patil, et al., Synthesis of some new thieno[3,4-d]pyrimidines and their C-nucleosides, Journal of Heterocyclic Chemistry, 1993, pp. 509-515, vol. 30, No. 2.
Perrone, et al., Application of the Phosphoramidate ProTide Approach to 4'-Azidouridine Confers Sub-micromolar Potency versus Hepatitis C Virus on an Inactive Nucleoside, Journal of Medicinal Chemistry, 2007, pp. 1840-1849, vol. 50, No. 8.
Peru Patent Office, Office Action in PE Application No. 1464, dated Sep. 12, 2013.
Piccirilli, et al., A Direct Route to 3-(D-Ribofuranosyl)pyridine Nucleosides, Helvetica Chimica Acta, 1991, pp. 397-406, vol. 74.
Pierra, et al., Synthesis and Pharmacokinetics of Valopicitabine (NM283), and Efficient Prodrug of the Potent Anti-HCV Agent 2'-C-Methylcytidine, Journal of Medicinal Chemistry, 2006, pp. 6614-6620, vol. 49, No. 22.
Poduch, et al., Design of Inhibitors of Orotidine Monophosphate Decarboxylase Using Bioisosteric Replacement and Determination of Inhibition Kinetics, Journal of Medicinal Chemistry, 2006, pp. 4937-4945, vol. 49, No. 16.
Puech, et al., Intracellular Delivery of Nucleoside Monophosphates through a Reductase-mediated Activation Process, Antiviral Research, 1993, pp. 155-174, vol. 22, No. 4.
Ramasamy, et al., Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor, J. Med. Chem., 1986, pp. 2231-2235, vol. 29, No. 11.
Rao, et al., C-Glycosylation of Substituted Heterocycles under Friedel-Crafts Conditions (I): A Two-Step Synthesis of the Thieno[3,4-d]Pyrimidine C-Nucleoside Analog of Inosine, Tetrahedron Letters, 1988, pp. 3537-3540, vol. 29, No. 29.
Reddy, et al., Stereoselective Synthesis of Nucleoside Monophosphate HepDirectTM Prodrugs, Tet. Letters, 2005, pp. 4321-4324, vol. 46.
Schul, et al., A Dengue Fever Viremia Model in Mice Shows Reduction in Viral Replication and Suppression of the Inflammatory Response after Treatment with Antiviral Drugs, Journal of Infectious Diseases, 2007, pp. 665-674, vol. 195.
Schultz, Prodrugs of Biologically Active Phosphate Esters, Bioorganic & Medicinal Chemistry, 2003, pp. 885-898, vol. 11.
Scott, et al., Interferon-a-2b Plus Ribavirin: A Review of its Use in the Management of Chronic Hepatitis C, Drugs, 2002, pp. 507-556, vol. 62, No. 3.
Shekunov, et al., Crystallization processes in pharmaceutical technology and drug delivery design, Journal of Crystal Growth, 2000, pp. 122-136, vol. 211.
Silverman et al., The Organic Chemistry of Drug Design and Drug Action, 1992, pp. 19-23.
Silverman, The Organic Chemistry of Drug Design and Drug Action, 2nd Ed., 2004, pp. 29-34.
Srivastav, et al., Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'—dideoxyribose Pyrimidine Nucleoside Analogues against Duck Hepatitis B Virus (DHBV) and Human Hepatitis B Virus (HBV) Replication, Journal of Medicinal Chemistry, 2010, pp. 7156-7166, vol. 53, No. 19.
Taiwan Patent Office, Office Action with Search Report for TW Patent Application No. 099131868, dated May 22, 2014.
Taiwan Patent Office, Office Action with Search Report for TW Patent Application No. 102115415, dated May 15, 2014.
Tapia, et al., Combination of a Mutagenic Agent with a Reverse Transcriptase Inhibitor Results n Systematic Inhibition of HIV-1 Infection, Virology, 2005, pp. 1-8, vol. 338.
Uchiyama, et al., O-selective Phosphorylation of Nucleosides without N-protection, J. Org. Chem., Jan. 1, 1993, vol. 58, No. 2.
Ukraine Patent Office, Second Office Action for UA Patent Application No. 2011 10568, dated Aug. 11, 2014.
United States Patent and Trademark Office, Final Rejection for U.S. Appl. No. 12/886,248, dated Aug. 21, 2014.
United States Patent and Trademark Office, Notice of Allowance for U.S. Appl. No. 13/649,511, dated Feb. 13, 2014.
United States Patent and Trademark Office, Notice of Allowance for U.S. Appl. No. 13/649,511, dated Jun. 3, 2014.
United States Patent and Trademark Office, Notice of Allowance for U.S. Appl. No. 12/428,176, dated Apr. 12, 2011.
United States Patent and Trademark Office, Notice of Allowance for U.S. Appl. No. 12/428,176, dated Jan. 6, 2011.
United States Patent and Trademark Office, Notice of Allowance for U.S. Appl. No. 12/428,234, dated Apr. 7, 2011.
United States Patent and Trademark Office, Notice of Allowance for U.S. Appl. No. 12/702,957, dated Apr. 26, 2011.
United States Patent and Trademark Office, Notice of Allowance for U.S. Appl. No. 12/885,917, dated Feb. 17, 2011.
United States Patent and Trademark Office, Notice of Allowance for U.S. Appl. No. 13/050,820, dated Jan. 31, 2013.

(56) References Cited

OTHER PUBLICATIONS

United States Patent and Trademark Office, Notice of Allowance for U.S. Appl. No. 13/117,060, dated Aug. 10, 2012.
United States Patent and Trademark Office, Notice of Allowance for U.S. Appl. No. 13/117,060, dated Nov. 28, 2012.
United States Patent and Trademark Office, Notice of Allowance for U.S. Appl. No. 13/196,117, dated Jul. 16, 2012.
United States Patent and Trademark Office, Notice of Allowance for U.S. Appl. No. 13/196,117, dated Mar. 27, 2012.
United States Patent and Trademark Office, Office Action (Restriction Requirement) for U.S. Appl. No. 12/886,248, dated Sep. 14, 2012.
United States Patent and Trademark Office, Office Action for U.S. Appl. No. 14/613,719, dated Jul. 21, 2016.
United States Patent and Trademark Office, Office Action for U.S. Appl. No. 14/613,719, dated Nov. 4, 2016.
United States Patent and Trademark Office, Office Action for U.S. Appl. No. 12/428,234, dated Dec. 23, 2010.
United States Patent and Trademark Office, Office Action for U.S. Appl. No. 12/702,957, dated Dec. 23, 2010.
United States Patent and Trademark Office, Office Action for U.S. Appl. No. 12/886,248, dated Mar. 4, 2013.
United States Patent and Trademark Office, Office Action for U.S. Appl. No. 12/886,248, dated Nov. 6, 2012.
United States Patent and Trademark Office, Office Action for U.S. Appl. No. 13/050,820, dated Mar. 27, 2012.
United States Patent and Trademark Office, Office Action for U.S. Appl. No. 13/050,820, dated Oct. 16, 2012.
United States Patent and Trademark Office, Office Action for U.S. Appl. No. 13/196,117 dated Sep. 23, 2011.
United States Patent and Trademark Office, Office Action for U.S. Appl. No. 13/649,511, dated Aug. 15, 2013.
United States Patent and Trademark Office, Office Action for U.S. Appl. No. 13/649,511, dated Jan. 22, 2013.
United States Patent and Trademark Office, Office Action for U.S. Appl. No. 13/813,886, dated Sep. 24, 2014.
United States Patent and Trademark Office, Pre-Appeal Brief for U.S. Appl. No. 14/613,719, dated Feb. 6, 2017.
United States Patent and Trademark Office, Pre-Appeal Decision for U.S. Appl. No. 14/613,719, dated Mar. 14, 2017.
Vaghefi, et al., Synthesis and Antiviral Activity of Certain Nucleoside 5'-Phosphonoformate Derivatives, Journal of Medicinal Chemistry, 1986, pp. 1389-1393, vol. 29, No. 8.
Vietnam Patent Office, Second Examination Report for VN Patent Application No. 1-2010-02939, dated Jul. 26, 2012.
Warren, et al., Therapeutic efficacy of the small molecule GS-5734 against Ebola virus in rhesus monkeys, Nature, 2016, pp. 381-385, vol. 531.
Wu, et al., Synthetic Methodologies for C-Nucleosides, Synthesis, 2004, pp. 1533-1553, vol. 10.
Yamanaka, et al., Metabolic Studies on BMS-200475, a New Antiviral Compound Active against Hepatitis B Virus, Antimicrobial Agents and Chemotherapy, 1999, p. 190, vol. 43, No. 1.

Yoshimura, et al., Synthesis and Biological Evaluation of 1'-C-Cyano-Pyrimidine Nucleosides, Nucleosides & Nucleotides, 1996, pp. 305-324, vol. 15, No. 1-3.
Zhang, et al., A Practical Synthesis of (2R)-3,5-di-O-benzoyl-2-fluoro-2-C-methyl-D-ribono-y-lactone, Tetrahedron: Asymmetry, 2009, pp. 305-312, vol. 20.
Barl, et al., The halogen/magnesium-exchange using iPrMgCl•LiCl and related exchange reagents, Heterocycles, Jan. 2014, pp. 827-844, vol. 88, No. 2.
Knaggs, et al. A QSAR Study Investigating the Effect of L-Alanine Ester Variation on the Anti-HIV Activity of Some Phosphoramidate Derivatives of d4T, 2000, pp. 2075-2078.
Lu, Chengping, Veterinary Microbiology 5th edition, Jan. 31, 2013, p. 431, China Agriculure Press (No English Translation available).
McGuigan, et al. Application of Phosphoramidate ProTide Technology Significantly Improves Antiviral Potency of Carbocyclic Adenosine Derivatives, 2006, pp. 7215-7226.
Porter, et al., Zika virus, drug discovery, and student projects, ScienceBlogs, Mar. 9, 2016, 7 pages.
Venkatachalam, T.K. et al. Effect of change in nucleoside structure on the activation and antiviral activity of phosphoramidate derivatives, 2005, pp. 5408-5423.
Bozza, Zika Outbreak, Brazil 2015, ISARIC, 2015, 28 pages.
Bullard-Feibelman, et al., The FDA-approved drug Sofosbuvir inhibits Zika Virus infection, Antiviral Res., Jan. 1, 2018, pp. 134-140, vol. 137.
Caira, Crystalline Polymorphism of Organic Compounds, Topics in Current Chemistry, 1998, pp. 163-208, vol. 198.
Cho, et al., Discovery of the First C-Nucleoside HCV Polymerase Inhibitor (GS-6620) with Demonstrated Antiviral Response in HCV Infected Patients, J. Med. Chem., 2014, pp. 1812-1825, vol. 57, No. 5.
Dai, et al., Synthesis of 2'-C-β-Fluoromethyluridine, Organic Letters, 2003, pp. 807-810, vol. 5, No. 6.
De Clercq, Antiviral Drugs: Current State of the Art, J. Clin. Virol., 2001, pp. 73-89, vol. 22, No. 1.
Sacramento, et al., The clinically approved antiviral drug Sofosbuvir inhibits Zika Virus replication, Nature, Jan. 18, 2017.
Siegel, Discovery and Synthesis of a Phosphoramidate Prodrug of a Pyrrolo[2,1-f][triazin-4-amino] Adenine C-Nucleoside(GS-5734) for the Treatment of Ebola and Emerging Viruses, J. Med. Chem., Jan. 26, 2017, 51 pages.
European Patent Office, International Search Report and Written Opinion for PCT International Application No. PCT/US2017/028251, dated Sep. 13, 2017, 22 pages.
European Patent Office, International Search Report and Written Opinion for PCT International Application No. PCT/US2018/022166, dated May 25, 2018, 13 pages.
European Patent Office, International Search Report and Written Opinion for PCT International Application No. PCT/US2018/029974, dated Sep. 18, 2018, 21 pages.
International Bureau of WIPO, International Preliminary Report on Patentability for PCT/US2018/041482, dated Jan. 23, 2020, 11 pages.

\* cited by examiner

COMPOSITIONS COMPRISING AN RNA POLYMERASE INHIBITOR AND CYCLODEXTRIN FOR TREATING VIRAL INFECTIONS

CROSS REFERENCE TO RELATED APPLICATIONS

This application claims priority to U.S. Provisional Application No. 62/530,971, filed Jul. 11, 2017, which is incorporated herein in its entirety for all purposes.

FIELD

Provided are pharmaceutical compositions suitable for treating viral infections such as Arenaviridae, Coronaviridae, Filoviridae, Flaviviridae, or Paramyxoviridae viral infections. In particular, formulations comprising Compound 1, or a pharmaceutically acceptable salt thereof, cyclodextrin and, optionally, pH adjusting agents.

BACKGROUND

Preventing or treating some Arenaviridae, Coronaviridae, Filoviridae, Flaviviridae, and Paramyxoviridae viral infections present challenges due to a lack of vaccine or postexposure treatment modality for preventing or managing infections caused by viruses from these families. In some cases, patients only receive supportive therapy such as electrolyte and fluid balancing, oxygen, blood pressure maintenance, or treatment for secondary infections.

The compound (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate, referred to herein as Compound 1, is known to exhibit antiviral properties against Arenaviridae, Coronaviridae, Filoviridae, and Paramyxoviridae viruses as described in Warren, T. et al., Nature (2016) 531:381-385, and antiviral activities against Flaviviridae viruses as described in co-pending International Publication No. WO 2017/184668. There is a need to administer Compound 1 parenterally to certain patients, however, Compound 1 is relatively insoluble and chemically unstable in aqueous media, thus there is a need to develop a composition comprising Compound 1, or a pharmaceutically acceptable salt thereof, that exhibits improved solubility, improved usability for parenteral administration, and sufficient room-temperature and elevated temperature stability to avoid the use of cold-chain for transport and/or storage.

Certain solubilizers may be used to improve the solubility of a compound to form a composition capable of being administered parenterally, however such solubilizers may have certain undesirable effects (Stella, et. al. Toxicologic Pathology (2008), Vol 36, Number 1, pages 30-42). For example, a formulation including polysorbate 80 may have potential hemodynamic effects, tubing limitations, extractables and leachables from tubing, limitations on stoppers, potential for precipitation upon dilution, or issues with adaptability for pediatric use. As another example, beta-cyclodextrin derivatives are known to have certain physiological effects on kidneys, thus there is also a need to limit the amount of such solubilizers in a pharmaceutical formulation. The present disclosure provides a composition comprising Compound 1, or a pharmaceutically acceptable salt thereof, that exhibits improved solubility and/or improved usability for parenteral administration and limits the amount of beta-cyclodextrin derivatives.

SUMMARY

The present disclosure provides a composition comprising (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate (Compound 1), or a pharmaceutically acceptable salt thereof, cyclodextrin, and, optionally, pH adjusting agents.

The present disclosure provides a composition comprising

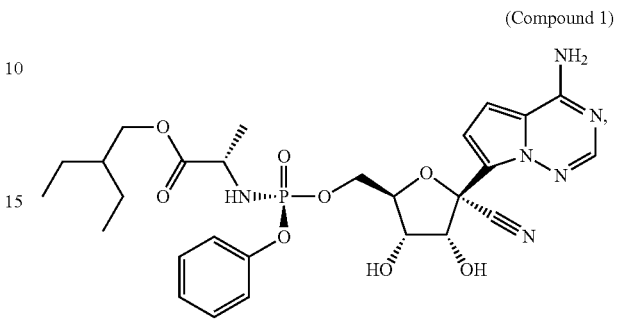

(Compound 1)

or a pharmaceutically acceptable salt thereof, cyclodextrin, and, optionally, pH adjusting agents.

DETAILED DESCRIPTION

I. General

The present invention includes a composition of Compound 1 and a cyclodextrin, such as betadex-sulfobutylether sodium, that is surprisingly stable at room temperature. The composition is substantially free of water following a dehydration or lyophilization process. The lyophilized composition can be prepared by suspending a crystalline form of Compound 1 in an acidic solution of betadex-sulfobutylether sodium, and subsequently adjusting the pH to between 3 to 4, to produce a solution that surprisingly maintains the complexation between Compound 1 and the betadex-sulfobutylether sodium, and lyophilizing the solution. The neutralized mixture is then lyophilized.

II. Definitions (S)-2-Ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate (Compound 1). Compound 1 is a viral RNA polymerase inhibitor with antiviral properties against Arenaviridae, Coronaviridae, Filoviridae, Flaviviridae, and Paramyxoviridae viruses. It has the following formula, as disclosed in PCT Publication No. WO2016/069826:

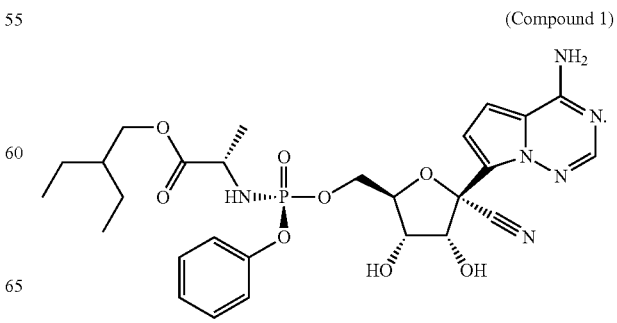

(Compound 1)

The IUPAC name for Compound 1 is (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate. The CAS Registry Number for Compound 1 is 1809249-37-3.

Figure 1:
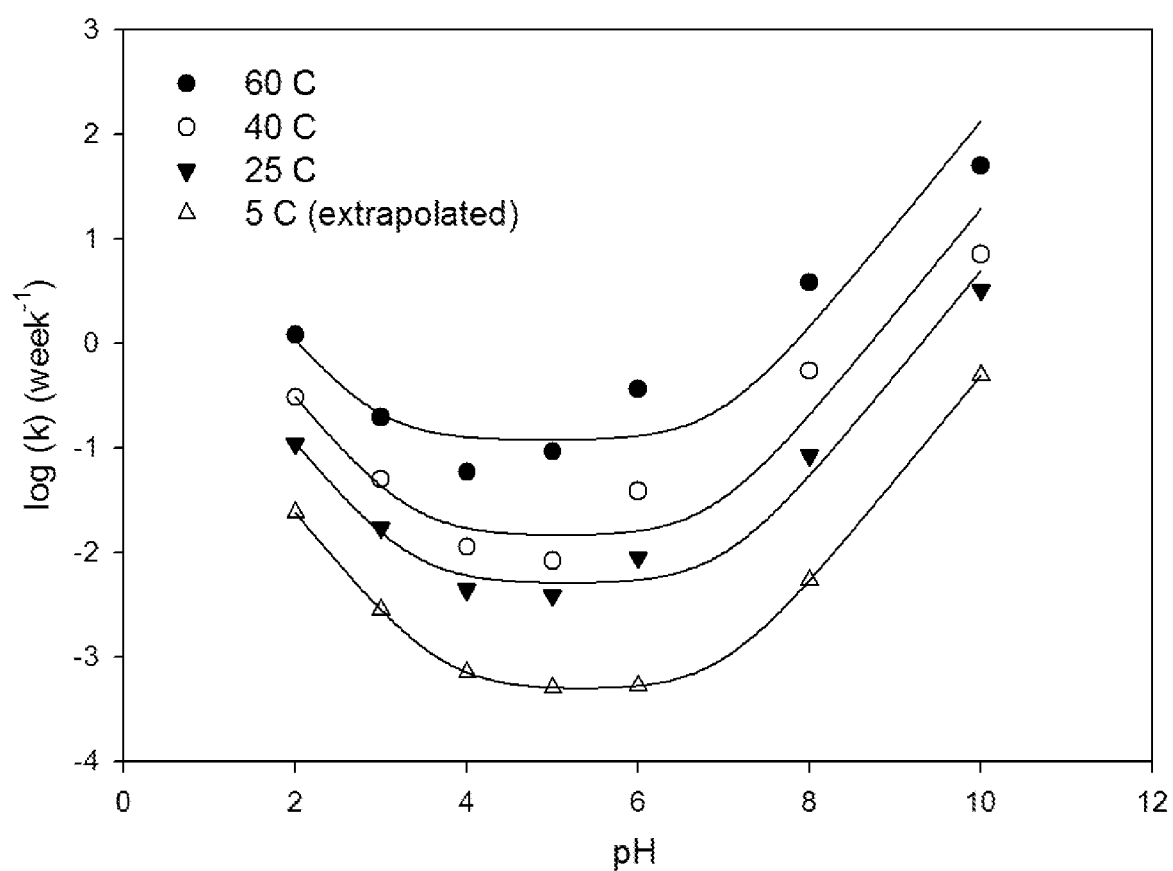
FIG. 1: pH Stability for Compound 1.
Figure 2:
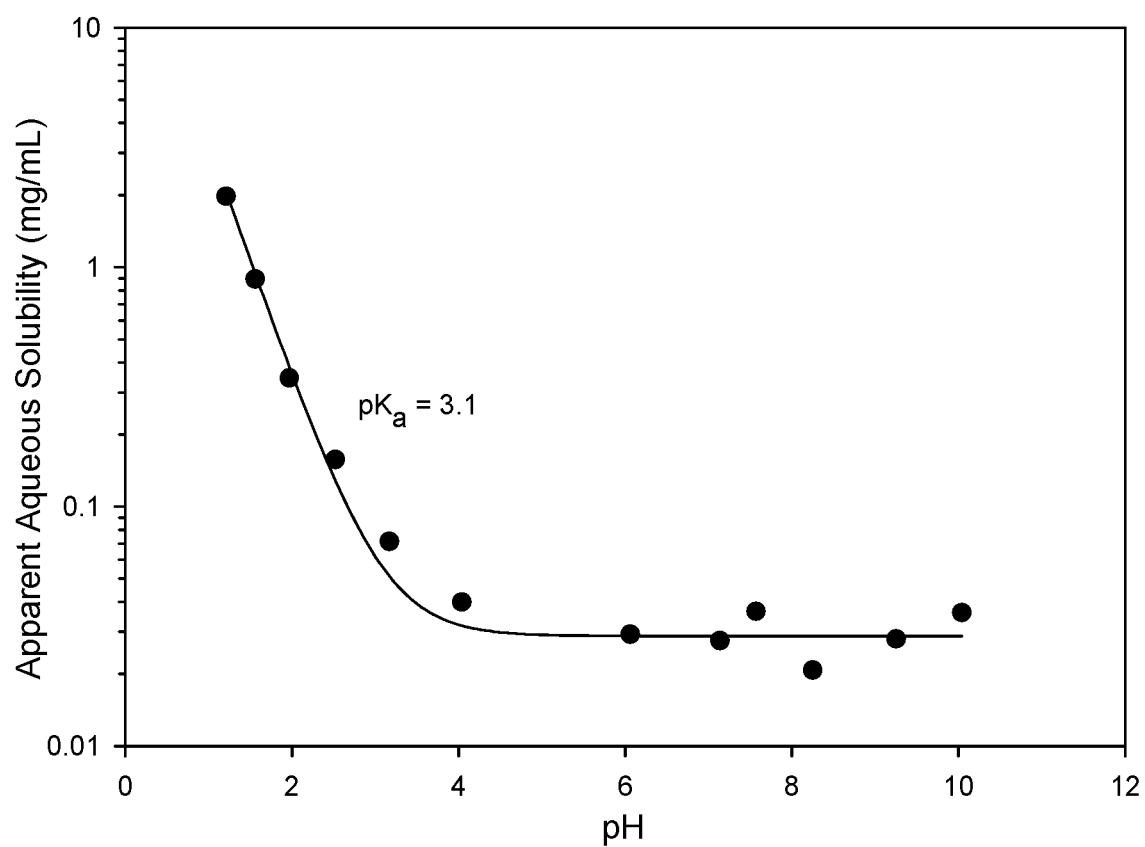
FIG. 2: pH Solubility Profile for Compound 1.

The stability of Compound 1 was determined by monitoring the concentration of Compound 1 in solution by liquid chromatography at various storage conditions. The stability results are shown in FIG. 1. Compound 1 is most stable in solution between about pH 4 and 5. The solubility of Compound 1 between pH 1 and 10 was determined by quantitatively measuring the concentration of Compound 1 in solution at various pH conditions by liquid chromatography. The solubility results are shown in FIG. 2. The solubility of Compound 1 increases at or below pH 4.

Cyclodextrin. Cyclodextrin is a chemical family of cyclic compound typically having 6, 7, or 8 sugar units. A cyclodextrin comprising 6 sugar units is an alpha-cyclodextrin (α-cyclodextrin). A cyclodextrin comprising 7 sugar units is a beta-cyclodextrin (β-cyclodextrin). A cyclodextrin comprising 8 sugar units is a gamma-cyclodextrin (γ-cyclodextrin).

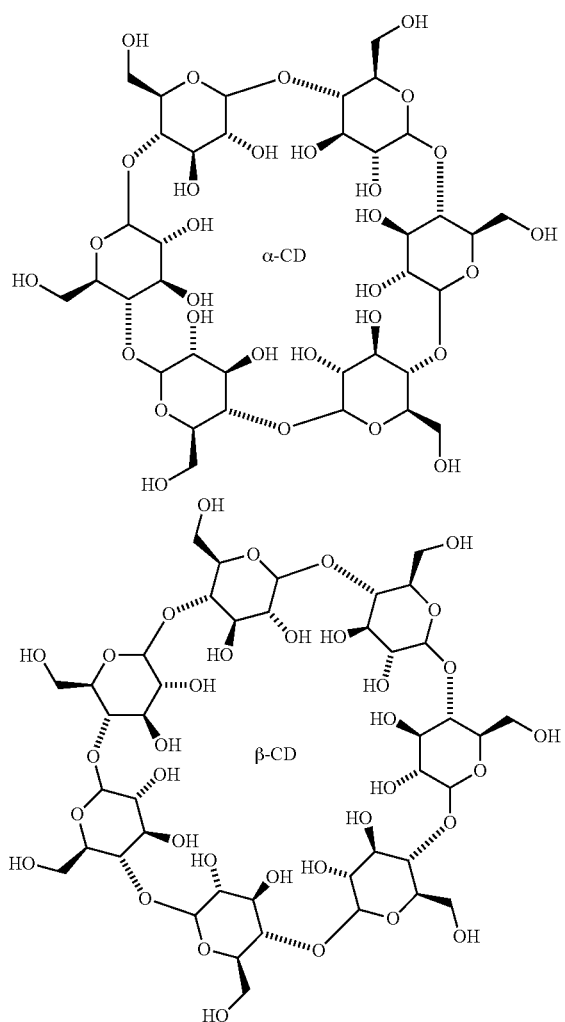

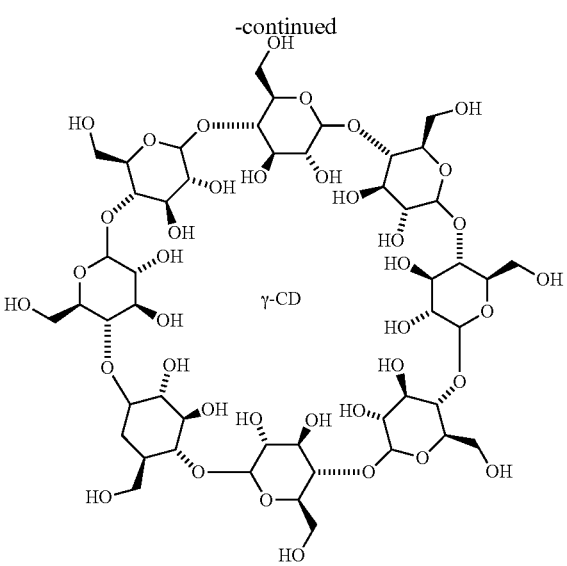

Cyclodextrin derivatives are cyclodextrins where some of the —OH groups are modified to —OR groups. Non-limiting examples of cyclodextrin derivatives include cyclodextrins where —OH groups are modified to —OR wherein each R is independently alkyl, hydroxyalkyl, glucosyl or maltosyl groups, or —(CH$_2$)$_4$SO$_3^-$Na$^+$.

Non-limiting examples of commercial cyclodextrin derivatives include CAPTISOL®, CAVITRON®, DEXOLVE-7®, and KLEPTOSE®. CAPTISOL® (herein referred to as Captisol) is a registered trademark of Ligand Corporation. Captisol refers to sulfobutylalkylether-beta-cyclodextrin sold by or licensed by Ligand Pharmaceuticals. CAVITRON® (herein referred to as Cavitron) is a registered trademark of Wacker Chemie AG. Cavitron is an excipient obtained by the substitution of hydroxyl groups on native cyclodextrins to make hydroxypropyl-beta-cyclodextrins (HPBCD), a process that significantly enhance their solubility and makes them more suitable for drug solubilization. DEXOLVE-7® (herein referred to as Dexolve-7) is a registered trademark of CycloLabs Limited. Dexolve-7 is sulfobutylalkylether-beta-cyclodextrin sodium salt, an excipient used in pharmaceutical formulations to improve solubility. KLEPTOSE® (herein referred to as Kleptose) is a registered trademark of Roquette Pharmaceuticals, Geneva, Ill., USA. Kleptose is a brand of hydroxypropyl-beta-cyclodextrin.

In some embodiments, "cyclodextrin" refers to beta-cyclodextrin derivatives selected from the group consisting of sulfobutylalkylether-beta-cyclodextrin, betadex-sulfobutylether sodium, and hydroxypropyl-beta-cyclodextrin. In some embodiments, "cyclodextrin" refers to sulfobutylalkylether-beta-cyclodextrin. In some embodiments, "cyclodextrin" refers to betadex-sulfobutylether sodium. In some embodiments, "cyclodextrin" refers to hydroxypropyl-beta-cyclodextrin. In some embodiments, "cyclodextrin" refers to the formula

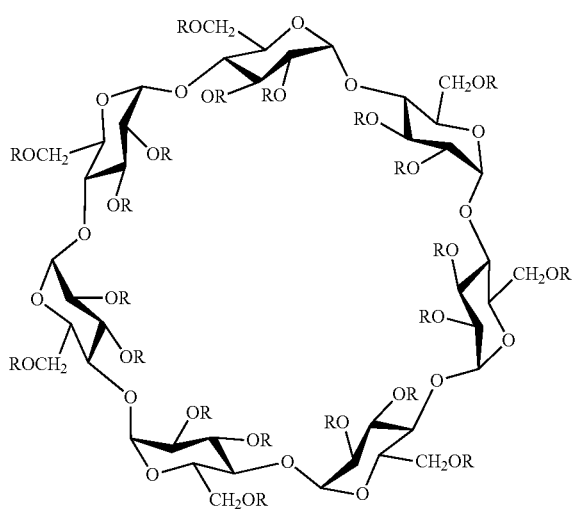

wherein R is —H or $CH_2CH_2CH_2CH_2SO_3^-Na^+$.

pH Adjusting Agent. pH adjusting agents are buffers, acids, and bases. "Acid" refers to a compound that is capable of donating a proton (W) under the Bronsted-Lowry definition, or is an electron pair acceptor under the Lewis definition. Acids useful in the present invention are Bronsted-Lowry acids that include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromice acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, triflouromethanesulfonic acid, camphorsulfonic acid, among others. "Base" refers to a compound capable of accepting a proton ($H^+$) under the Bronsted-Lowry definition, or is an electron-pair donor under the Lewis definition. Bases useful in the present invention that are Bronsted-Lowry bases include hydroxides such as lithium hydroxide, sodium hydroxide, potassium hydroxide, rubidium hydroxide, cesium hydroxide, magnesium hydroxide, strontium hydroxide, barium hydroxide, and others. Lewis bases include, but are not limited to, amines such as ammonia, trimethylamine, triethylamine, diisopropylethylamine (DIPEA or Hunig's Base), 1,8-diazabicycloundec-7-ene (DBU), 2,6-di-tert-butylpyridine, quinuclidine, and lithium di-isopropylamine (LDA), and nucleophilic bases such as butyl-lithium. Other bases are known to one of skill in the art. In some embodiments, the pH adjusting agents are NaOH and HCl. In some embodiments, the pH adjusting agent is NaOH. In some embodiments, the pH adjusting agent is HCl.

"Dehydrate" refers to the process of removing water from a sample via evaporation, sublimation, or a combination thereof. Evaporation refers to the transition of a substance from a liquid state to a gaseous state, and sublimation to the transition from a solid state directly to a gaseous state. Dehydration can occur at a variety of temperatures and pressures. When dehydration occurs below the freezing point of the sample, this is referred to as freeze-drying or lyophilizing, the process of removing water from a sample at low temperature and pressure.

The term "treatment" or "treating" means any administration of Compound 1 according to the present disclosure to a subject (e.g. human) having or susceptible to a condition or disease disclosed herein for the purpose of: 1) preventing or protecting against the disease or condition, that is, causing the clinical symptoms not to develop; 2) inhibiting the disease or condition, that is, arresting or suppressing the development of clinical symptoms; or 3) relieving the disease or condition that is causing the regression of clinical symptoms. In some embodiments, the term "treatment" or "treating" refers to relieving the disease or condition, i.e. which is causing the regression of clinical symptoms.

As used herein, the term "preventing" refers to the prophylactic treatment of a patient in need thereof. The prophylactic treatment can be accomplished by providing an appropriate dose of a therapeutic agent e.g. Compound 1, to a subject at risk of suffering from an ailment, thereby substantially averting onset of the ailment. The presence of a genetic mutation or the predisposition to having a mutation may not be alterable. However, prophylactic treatment (prevention) as used herein has the potential to avoid/ameliorate the symptoms or clinical consequences of having the disease engendered by such genetic mutation or predisposition.

"Subject" refers to animals such as mammals, including, but not limited to, primates (e.g., humans), cows, sheep, goats, horses, dogs, cats, rabbits, rats, mice and the like. In certain embodiments, the subject is a human.

The term "therapeutically effective amount", as used herein, is the amount of Compound 1, or a pharmaceutically acceptable salt thereof, present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the specific activity of the composition, the delivery device employed, the physical characteristics of the composition, its intended use, as well as animal considerations such as severity of the disease state, veterinarian cooperation, etc., and can readily be determined by one skilled in the art based upon the information provided herein.

"Safe water for injection", "water safe for infection" or "sterile water for injection" refers to a water solution for combining with one or more drugs requiring dilution or dissolution prior to administration to the subject. The water for injection is sterile and stored in a glass vial of Type I or II borosilicate glass, or other suitable container. The water for injection does not include any other components, such as stabilizers, antimicrobial agents, buffer, etc.

The term "normal saline" means a water solution containing 0.9% (w/v) NaCl.

The term "hypertonic saline" means a water solution containing greater than 0.9% (w/v) NaCl. For example, 3% hypertonic saline would contain 3% (w/v) NaCl.

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

III. Formulations

All compositions described here contain Compound 1, or a pharmaceutically acceptable salt thereof, cyclodextrin, and, optionally, pH adjusting agents.

In some embodiments, a composition comprising Compound 1, or a pharmaceutically acceptable salt thereof, cyclodextrin, and, optionally, pH adjusting agents.

In some embodiments, a composition comprising

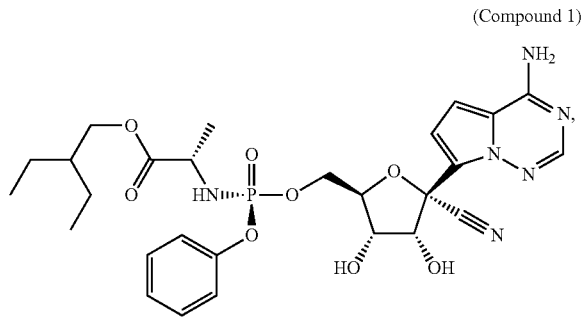 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

(Compound 1)

or a pharmaceutically acceptable salt thereof, cyclodextrin, and, optionally, pH adjusting agents.

In some embodiments, a composition comprising Compound 1, or a pharmaceutically acceptable salt thereof, and beta-cyclodextrin, and, optionally, pH adjusting agents.

In some embodiments, an antiviral composition comprising Compound 1, or a pharmaceutically acceptable salt thereof, and beta-cyclodextrin, and, optionally, pH adjusting agents.

In some embodiments, a composition comprising Compound 1, or a pharmaceutically acceptable salt thereof, and beta-cyclodextrin, and, optionally, pH adjusting agents, wherein the beta cyclodextrin is sulfobutylalkylether-beta-cyclodextrin, betadex-sulfobutylether sodium, or hydroxypropyl-beta-cyclodextrin.

In some embodiments, a composition comprising Compound 1, or a pharmaceutically acceptable salt thereof, and beta-cyclodextrin, and, optionally, pH adjusting agents, wherein the beta cyclodextrin is betadex-sulfobutylether sodium.

Solution Composition

In some embodiments, the composition also includes water to form a solution composition. The water can be any suitable water, such as distilled water or water safe for injection. In some embodiments, the water can be water safe for injection.

In some embodiments, a composition comprising Compound 1, or a pharmaceutically acceptable salt thereof, and beta-cyclodextrin, and, optionally, pH adjusting agents, wherein the pH adjusting agents are NaOH and HCl.

Any suitable number of pH adjusting agents can be used in the composition of the present invention. For example, the composition can includes, 1, 2, 3, 4 or more pH adjusting agents. In some embodiments, the composition includes at least one pH adjusting agent. In some embodiments, the composition includes at least 2 pH adjusting agents. When more than 1 pH adjusting agent is used, the pH adjusting agents can be acids, bases, or a mixture thereof. In some embodiments, a first pH adjusting agent includes an acid, and a second pH adjusting agent includes a base.

In some embodiments, the solution composition includes Compound 1, or a pharmaceutically acceptable salt thereof, beta-cyclodextrin, and at least one pH adjusting agent. In some embodiments, the solution composition includes Compound 1, or a pharmaceutically acceptable salt thereof, beta-cyclodextrin, and at least two pH adjusting agent. In some embodiments, the solution composition includes Compound 1, or a pharmaceutically acceptable salt thereof, beta-cyclodextrin, and the pH adjusting agents HCl and NaOH.

The solution composition has a pH of less than 7, preferably less than about 6, 5, or 4. The pH of the solution composition can be from 1 to 6, 2 to 5, or 3 to 4. For example, the pH of the solution composition can be about 3.1, 3.2, 3.3, 3.4, 3.5, 3.6, 3.7, 3.8, or about 3.9. In some embodiments, the solution composition has a pH of from 3 to 4. In some embodiments, the solution composition has a pH of about 3.5.

In some embodiments, an antiviral composition comprising Compound 1, or a pharmaceutically acceptable salt thereof, and beta-cyclodextrin, and, optionally, pH adjusting agents, wherein the pH adjusting agents are NaOH and HCl.

In some embodiments, a composition comprising 90 mg to 175 mg of Compound 1, or a pharmaceutically acceptable salt thereof, and beta-cyclodextrin, and, optionally, pH adjusting agents. In some embodiments, a composition comprising 90 mg to 110 mg of Compound 1, or a pharmaceutically acceptable salt thereof, and beta-cyclodextrin, and, optionally, pH adjusting agents. In some embodiments, a composition comprising 145 mg to 165 mg of Compound 1, or a pharmaceutically acceptable salt thereof, and beta-cyclodextrin, and, optionally, pH adjusting agents. In some embodiments, a composition comprising 100 mg of Compound 1, or a pharmaceutically acceptable salt thereof, and beta-cyclodextrin, and, optionally, pH adjusting agents. In some embodiments, a composition comprising 150 mg of Compound 1, or a pharmaceutically acceptable salt thereof, and beta-cyclodextrin, and, optionally, pH adjusting agents.

In some embodiments, a composition comprising 90 mg to 175 mg of Compound 1, or a pharmaceutically acceptable salt thereof, and beta-cyclodextrin, and, optionally, pH adjusting agents, wherein the pH adjusting agents are NaOH and HCl. In some embodiments, a composition comprising 90 mg to 110 mg of Compound 1, or a pharmaceutically acceptable salt thereof, and beta-cyclodextrin, and, optionally, pH adjusting agents, wherein the pH adjusting agents are NaOH and HCl. In some embodiments, a composition comprising 145 mg to 165 mg of Compound 1, or a pharmaceutically acceptable salt thereof, and beta-cyclodextrin, and, optionally, pH adjusting agents, wherein the pH adjusting agents are NaOH and HCl. In some embodiments, a composition comprising 100 mg of Compound 1, or a pharmaceutically acceptable salt thereof, and beta-cyclodextrin, and, optionally, pH adjusting agents, wherein the pH adjusting agents are NaOH and HCl. In some embodiments, a composition comprising 150 mg of Compound 1, or a pharmaceutically acceptable salt thereof, and beta-cyclodextrin, and, optionally, pH adjusting agents, wherein the pH adjusting agents are NaOH and HCl.

In some embodiments, the cyclodextrin is present at about 5% to 30% w/v. In some embodiments, the cyclodextrin is present at about 10% to 25% w/v. In some embodiments, the cyclodextrin is present at about 14% to 21% w/v. In some embodiments, the cyclodextrin is present at about 15% w/v. In some embodiments, the cyclodextrin is present at about 20% w/v. In some embodiments, the cyclodextrin is present at 15% w/v. In some embodiments, the cyclodextrin is present at 20% w/v.

In some embodiments, the beta-cyclodextrin is present at about 5% to 30% w/v. In some embodiments, the beta-cyclodextrin is present at about 10% to 25% w/v. In some embodiments, the beta-cyclodextrin is present at about 14% to 21% w/v. In some embodiments, the beta-cyclodextrin is present at about 15% w/v. In some embodiments, the beta-cyclodextrin is present at about 20% w/v. In some embodiments, the beta-cyclodextrin is present at 15% w/v. In some embodiments, the beta-cyclodextrin is present at 20% w/v.

In some embodiments, Compound 1 is present at about 1.0 to 10.0 mg/mL. In some embodiments, Compound 1 is present at about 4.0 to 8.0 mg/mL. In some embodiments, Compound 1 is present at about 5.0 to 7.0 mg/mL. In some embodiments, Compound 1 is present at about 5.0 mg/mL. In some embodiments, Compound 1 is present at about 6.7 mg/mL. In some embodiments, Compound 1 is present at 5.0 mg/mL. In some embodiments, Compound 1 is present at 6.7 mg/mL.

In some embodiments, a composition comprising Compound 1, or a pharmaceutically acceptable salt thereof, and beta-cyclodextrin, and, optionally, pH adjusting agents, wherein Compound 1 is present at about 4.0 to 8.0 mg/mL and the beta-cyclodextrin is present at about 5% to 30% w/v. In some embodiments, a composition comprising Compound 1, or a pharmaceutically acceptable salt thereof, and beta-cyclodextrin, and, optionally, pH adjusting agents, wherein Compound 1 is present at about 4.0 to 8.0 mg/mL and the beta-cyclodextrin is present at about 10% to 25% w/v. In some embodiments, a composition comprising Compound 1, or a pharmaceutically acceptable salt thereof, and beta-cyclodextrin, and, optionally, pH adjusting agents, wherein Compound 1 is present at about 4.0 to 8.0 mg/mL and the beta-cyclodextrin is present at about 14% to 21% w/v.

In some embodiments, a composition comprising Compound 1, or a pharmaceutically acceptable salt thereof, and beta-cyclodextrin, and, optionally, pH adjusting agents, wherein Compound 1 is present at about 5.0 to 7.0 mg/mL and the beta-cyclodextrin is present at about 5% to 30% w/v. In some embodiments, a composition comprising Compound 1, or a pharmaceutically acceptable salt thereof, and beta-cyclodextrin, and, optionally, pH adjusting agents, wherein Compound 1 is present at about 5.0 to 7.0 mg/mL and the beta-cyclodextrin is present at about 10% to 25% w/v. In some embodiments, a composition comprising Compound 1, or a pharmaceutically acceptable salt thereof, and beta-cyclodextrin, and, optionally, pH adjusting agents, wherein Compound 1 is present at about 5.0 to 7.0 mg/mL and the beta-cyclodextrin is present at about 14% to 21% w/v.

In some embodiments, a composition comprising Compound 1, or a pharmaceutically acceptable salt thereof, and beta-cyclodextrin, and, optionally, pH adjusting agents, wherein Compound 1 is present at about 5.0 mg/mL and the beta-cyclodextrin is present at about 15% w/v. In some embodiments, a composition comprising Compound 1, or a pharmaceutically acceptable salt thereof, and beta-cyclodextrin, and, optionally, pH adjusting agents, wherein Compound 1 is present at about 6.7 mg/mL and the beta-cyclodextrin is present at about 20% w/v.

In some embodiments, a composition comprising Compound 1, or a pharmaceutically acceptable salt thereof, and beta-cyclodextrin, and, optionally, pH adjusting agents, wherein Compound 1 is present at about 5.0 mg/mL and the beta-cyclodextrin is present at about 15% w/v further comprising water for injection. In some embodiments, a composition comprising Compound 1, or a pharmaceutically acceptable salt thereof, and beta-cyclodextrin, and, optionally, pH adjusting agents, wherein Compound 1 is present at about 6.7 mg/mL and the beta-cyclodextrin is present at about 20% w/v further comprising water for injection.

In some embodiments, a vial comprising Compound 1, or a pharmaceutically acceptable salt thereof, and beta-cyclodextrin, and, optionally, pH adjusting agents, wherein Compound 1 is present at about 5.0 mg/mL and the beta-cyclodextrin is present at about 15% w/v further comprising water for injection. In some embodiments, a vial comprising Compound 1, or a pharmaceutically acceptable salt thereof, and beta-cyclodextrin, and, optionally, pH adjusting agents, wherein Compound 1 is present at about 6.7 mg/mL and the beta-cyclodextrin is present at about 20% w/v further comprising water for injection.

In some embodiments, a lyophilized composition comprising Compound 1, or a pharmaceutically acceptable salt thereof, and beta-cyclodextrin, and, optionally, pH adjusting agents, wherein Compound 1 is present at about 5.0 mg/mL and the beta-cyclodextrin is present at about 15% w/v. In some embodiments, a lyophilized composition comprising Compound 1, or a pharmaceutically acceptable salt thereof, and beta-cyclodextrin, and, optionally, pH adjusting agents, wherein Compound 1 is present at about 6.7 mg/mL and the beta-cyclodextrin is present at about 20% w/v. In some embodiments, a lyophilized composition comprising about 90 to 175 mg Compound 1, or a pharmaceutically acceptable salt thereof, and beta-cyclodextrin, and, optionally, pH adjusting agents, wherein the beta-cyclodextrin is present at about 15 to 20% w/v. In some embodiments, a lyophilized composition comprising about 100 mg Compound 1, or a pharmaceutically acceptable salt thereof, and beta-cyclodextrin, and, optionally, pH adjusting agents, wherein the beta-cyclodextrin is present at about 15 to 20% w/v. In some embodiments, a lyophilized composition comprising about 150 mg Compound 1, or a pharmaceutically acceptable salt thereof, and beta-cyclodextrin, and, optionally, pH adjusting agents, wherein the beta-cyclodextrin is present at about 15 to 20% w/v.

In some embodiments, a composition comprising crystalline Compound 1, or a pharmaceutically acceptable salt thereof, and beta-cyclodextrin, and, optionally, pH adjusting agents, wherein crystalline Compound 1 is characterized by an X-ray powder diffraction (XRPD) pattern having at least three peaks selected from the group consisting of 22.3°, 16.2°, 22.5°, 13.8°, 12.7°, 16.9°, 10.6°, 14.5°, 24.3, 24.0°, 17.6°, 23.4°, 8.1°, 11.0°, 26.8°, 28.9°, 19.6°, 27.8°, 26.4°, 28.7°, 29.8°, 33.0°, 18.8°, 183°, 32.1°, 25.3°, 32.6°, 8.6°, 34.2°, 35.9°, 27.2°, 28.1°, 38.9°, 34.6°, 17.1°, 35.2°, 21.4°, 30.6°, 25.6°, 18.5°, 31.7°, 36.5°, and 37.1°±0.2° 2–θ.

Lyophilized Composition

The composition of the present invention also includes a lyophilized or dehydrated composition of Compound 1, or a pharmaceutically acceptable salt thereof, and cyclodextrin. In some embodiments, the present invention provides a lyophilized composition including Compound 1, or a pharmaceutically acceptable salt thereof, and cyclodextrin. The lyophilized composition can be in any suitable solid form, such as a powder.

Compound 1 can be present in the lyophilized composition in an amount from 1% to 10% (w/w), or from 1 to 5%, or from 2 to 4%, or from 3 to 4%, or from 3 to 3.5% (w/w). In some embodiments, the lyophilized composition includes Compound 1 in an amount from 1% to 10% (w/w). In some embodiments, the lyophilized composition include Compound 1 in an amount from 1% to 5% (w/w). In some embodiments, the lyophilized composition includes Compound 1 in an amount from 2% to 4% (w/w). In some embodiments, the lyophilized composition includes Compound 1 in an amount from 3% to 3.5% (w/w).

Compound 1 can be present in the lyophilized composition in an amount of about 1% (w/w), or 1.5, 2, 2.1, 2.2, 2.3, 2.4, 2.5, 2.6, 2.7, 2.8, 3.9, 3, 3.1, 3.2, 3.3, 3.4, 3.5, 3.6, 3.7, 3.8, 3.9, 4, 4.5, 5, 6, 7, 8, 9, or about 10% (w/w). In some embodiments, the lyophilized composition includes Compound 1 at about 3.2% (w/w).

Cyclodextrin can be present in the lyophilized composition in an amount from 90% to 99% (w/w), or from 95 to 99%, or from 96 to 98%, or from 96.5 to 97% (w/w). In some embodiments, the lyophilized composition includes cyclodextrin in an amount from 90% to 99% (w/w). In some embodiments, the lyophilized composition includes cyclodextrin in an amount from 95 to 99% (w/w). In some embodiments, the lyophilized composition includes cyclodextrin in an amount from 96 to 98% (w/w). In some embodiments, the lyophilized composition includes cyclodextrin in an amount from 96.5 to 97% (w/w).

Cyclodextrin can be present in the lyophilized composition in an amount of about 90% (w/w), or 91, 92, 93, 94, 95, 95.1, 95.2, 95.3, 95.4, 95.5, 95.6, 95.7, 95.8, 95.9, 96, 96.1, 96.2, 96.3, 96.4, 96.5, 96.6, 96.7, 96.8, 96.9, 97, 97.1, 97.2, 97.3, 97.4, 97.5, 97.6, 97.7, 97.8, 97.9, 98, or about 99% (w/w). In some embodiments, the lyophilized composition includes cyclodextrin at about 96.8% (w/w). In some embodiments, the lyophilized composition includes betadex-sulfobutylether sodium at about 96.8% (w/w). In some embodiments, the lyophilized composition includes Compound 1 at about 3.2% (w/w), and cyclodextrin at about 96.8% (w/w). In some embodiments, the lyophilized composition includes Compound 1 at about 3.2% (w/w), and betadex-sulfobutylether sodium at about 96.8% (w/w).

The lyophilized composition of the present invention can include Compound 1 in an amount from 1% to 10% (w/w), or from 1 to 5%, or from 2 to 4%, or from 3 to 4%, or from 3 to 3.5%, and cyclodextrin in an amount from 90% to 99% (w/w), or from 95 to 99%, or from 96 to 98%, or from 96.5 to 97% (w/w). In some embodiments, the lyophilized composition includes Compound 1 in an amount from 1% to 10% (w/w), and cyclodextrin in an amount from 90% to 99% (w/w). In some embodiments, the lyophilized composition include Compound 1 in an amount from 1% to 5% (w/w), and cyclodextrin in an amount from 95 to 99% (w/w). In some embodiments, the lyophilized composition includes Compound 1 in an amount from 2% to 4% (w/w), and cyclodextrin in an amount from 96 to 98% (w/w). In some embodiments, the lyophilized composition includes Compound 1 in an amount from 3% to 3.5% (w/w), and cyclodextrin in an amount from 96.5 to 97% (w/w).

In some embodiments, the lyophilized composition includes Compound 1 at about 3.2% (w/w) and cyclodextrin in an amount of about 96.8% (w/w). In some embodiments, the lyophilized composition includes Compound 1 at 3.2% (w/w) and cyclodextrin in an amount of 96.8% (w/w). In some embodiments, the lyophilized composition consists essentially of Compound 1 at about 3.2% (w/w) and cyclodextrin in an amount of about 96.8% (w/w). In some embodiments, the lyophilized composition consists essentially of Compound 1 at 3.2% (w/w) and cyclodextrin in an amount of 96.8% (w/w).

In some embodiments, the lyophilized composition includes Compound 1 at about 3.2% (w/w) and betadex-sulfobutylether sodium in an amount of about 96.8% (w/w). In some embodiments, the lyophilized composition includes Compound 1 at 3.2% (w/w) and betadex-sulfobutylether sodium in an amount of 96.8% (w/w). In some embodiments, the lyophilized composition consists essentially of Compound 1 at about 3.2% (w/w) and betadex-sulfobutylether sodium in an amount of about 96.8% (w/w). In some embodiments, the lyophilized composition consists essentially of Compound 1 at 3.2% (w/w) and betadex-sulfobutylether sodium in an amount of 96.8% (w/w).

The cyclodextrin of the lyophilized composition can include any suitable cyclodextrin as described above. For example, the cyclodextrin can be a beta-cyclodextrin, such as sulfobutylalkylether-beta-cyclodextrin, betadex-sulfobutylether sodium, or hydroxypropyl-beta-cyclodextrin. In some embodiments, the lyophilized composition includes a beta-cyclodextrin. In some embodiments, the lyophilized composition includes sulfobutylalkylether-beta-cyclodextrin, betadex-sulfobutylether sodium, or hydroxypropyl-beta-cyclodextrin. In some embodiments, the lyophilized composition includes betadex-sulfobutylether sodium.

In some embodiments, a composition comprising Compound 1, or a pharmaceutically acceptable salt thereof, and beta-cyclodextrin, and, optionally, pH adjusting agents, wherein Compound 1 is 3%±1% w/w and beta-cyclodextrin is 97%±1% w/w. In some embodiments, a composition comprising Compound 1, or a pharmaceutically acceptable salt thereof, and beta-cyclodextrin, and, optionally, pH adjusting agents, wherein Compound 1 is 3%±0.5% w/w and beta-cyclodextrin is 97%±0.5% w/w. In some embodiments, a composition comprising Compound 1, or a pharmaceutically acceptable salt thereof, and beta-cyclodextrin, and, optionally, pH adjusting agents, wherein Compound 1 is about 3.2% w/w and beta-cyclodextrin is 96.8% w/w.

The lyophilized compositions of the present invention are surprisingly stable, showing relatively little impurity formation when tested at raised temperatures and relative humidity. For example, the purity of the lyophilized composition can be at least 95%, or 96, 97, 98, 99, 99.1, 99.2, 99.3, 99.4, 99.5, 99.6, 99.7, 99.8, or at least 99.9%. Thus, the lyophilized composition can have an impurity in the amount of less than 5%, or 4, 3, 2, 1, 0.9, 0.8, 0.7, 0.6, 0.5, 0.4, 0.3, 0.2, or less than 0.1%. In some embodiments, the lyophilized composition has less than about 1% AN via HPLC of impurity following one or more of the following: (i) storage for 18 months at a temperature of about 25° C. (±1° C.) and a relative humidity of about 60% (±1%); (ii) storage for 18 months at a temperature of about 30° C. (±1° C.) and a relative humidity of about 75% (±1%); or (iii) storage for 6 months at a temperature of about 40° C. (±1° C.) and a relative humidity of about 75% (±1%). In some embodiments, the lyophilized composition has less than about 0.5% AN via HPLC of impurity following one or more of the following: (i) storage for 18 months at a temperature of about 25° C. (±1° C.) and a relative humidity of about 60% (±1%); (ii) storage for 18 months at a temperature of about 30° C. (±1° C.) and a relative humidity of about 75% (±1%); or (iii) storage for 6 months at a temperature of about 40° C. (±1° C.) and a relative humidity of about 75% (±1%).

The lyophilized composition can include various forms of Compound 1. For example, Compound 1 can be amorphous or crystalline, or a mixture thereof. In some embodiments, the lyophilized composition includes amorphous Compound 1.

The lyophilized composition can be contained in any suitable container, such as a sealed vial. In some embodiments, the present invention provides a sealed vial containing the lyophilized composition. In some embodiments, the present invention provides a sealed vial containing the lyophilized composition consisting essentially of Compound 1 at 3.2% (w/w) and betadex-sulfobutylether sodium in an amount of 96.8% (w/w).

Injectable Composition

The composition of the present invention also includes an injectable composition for administration to subjects and patients in need of treatment. The injectable composition includes the lyophilized composition described above, and water. In some embodiments, the present invention provides an injectable composition, including Compound 1:

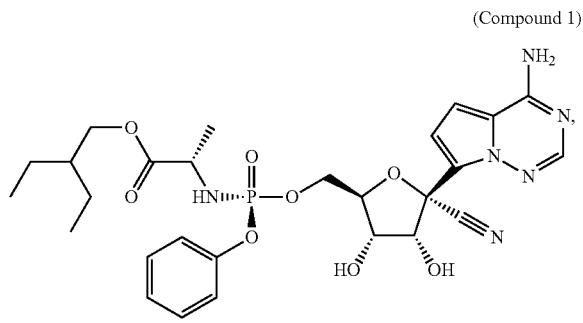 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

(Compound 1)

or a pharmaceutically acceptable salt thereof, in an amount from 0.1% to 10% w/v; cyclodextrin in an amount from 10% to 50% w/v; and water.

The cyclodextrin of the injectable composition can include any suitable cyclodextrin as described above. For example, the cyclodextrin can be a beta-cyclodextrin, such as sulfobutylalkylether-beta-cyclodextrin, betadex-sulfobutylether sodium, or hydroxypropyl-beta-cyclodextrin. In some embodiments, the injectable composition includes a beta-cyclodextrin. In some embodiments, the injectable composition includes sulfobutylalkylether-beta-cyclodextrin, betadex-sulfobutylether sodium, or hydroxypropyl-beta-cyclodextrin. In some embodiments, the injectable composition includes betadex-sulfobutylether sodium.

The water of the injectable composition can be any suitable type of water. For example, the water of the injectable composition can be water safe for injection.

The injectable composition include any suitable amount of Compound 1 from 0.1% to 10% w/v. For example, Compound 1 can be present in the injectable composition in an amount from 0.1% to 5% w/v, 0.1 to 4, 0.1 to 3, 0.1 to 2, 0.1 to 1, 0.2 to 0.8, 0.3 to 0.7, or 0.4% to 0.6% w/v. Compound 1 can be present in the injectable composition in an amount of about 0.1% w/v, or 0.2, 0.3, 0.4, 0.5, 0.6, 0.7, 0.8, 0.9, or about 1% w/v. In some embodiments, Compound 1 is present in the injectable composition in an amount of 0.1% to 10% w/v. In some embodiments, Compound 1 is present in the injectable composition in an amount of 0.1% to 1% w/v. In some embodiments, Compound 1 is present in the injectable composition in an amount of about 0.5% w/v.

The injectable composition include any suitable amount of Compound 1 from 0.1 to 100 mg/mL. For example, Compound 1 can be present in the injectable composition in an amount from 0.1 to 100 mg/mL, or 0.1 to 50, 0.5 to 10, 1 to 10, 2 to 8, 3 to 7, 4 to 6, or 4.5 to 5.5 mg/mL. Compound 1 can be present in the injectable composition in an amount of about 0.1 mg/mL, or 0.5, 1, 2, 2.5, 3, 3.5, 4, 4.5, 4.6, 4.7, 4.8, 4.9, 5, 5.1, 5.2, 5.3, 5.4, 5.5, 6, 6.5, 7, 7.5, 8, 8.5, 9, 9.5, 10, 15, 20 or 25 mg/mL. In some embodiments, Compound 1 is present in the injectable composition in an amount of 1 to 10 mg/mL. In some embodiments, Compound 1 is present in the injectable composition in an amount of 4 to 6 mg/mL. In some embodiments, Compound 1 is present in the injectable composition in an amount of about 5 mg/mL.

The injectable composition also includes cyclodextrin in any suitable amount from 5% to 50% w/v. The cyclodextrin can be present in the injectable composition in an amount of from 5% to 50% w/v, or 5 to 25, or 10% to 20% w/v. The cyclodextrin can be present in the injectable composition in an amount of about 5% w/v, or 6, 7, 8, 9, 10, 11, 12, 13, 14, 15, 16, 17, 18, 19, 20, 25, 30, 35, 40, 45, or 50% w/v. In some embodiments, the cyclodextrin is present in the injectable composition in an amount of 5% to 50% w/v. In some embodiments, the cyclodextrin is present in the injectable composition in an amount of 10% to 20% w/v. In some embodiments, the cyclodextrin is present in the injectable composition in an amount of about 15% w/v. In some embodiments, the betadex-sulfobutylether sodium is present in the injectable composition in an amount of about 15% w/v.

The injectable composition can include Compound 1 and the cyclodextrin in any suitable combination of amounts as described above. For example, The injectable composition can include Compound 1 in an amount from 0.1% to 5% w/v, 0.1 to 4, 0.1 to 3, 0.1 to 2, 0.1 to 1, 0.2 to 0.8, 0.3 to 0.7, or 0.4% to 0.6% w/v, and cyclodextrin in an amount of from 5% to 50% w/v, or 5 to 25, or 10% to 20% w/v. The injectable composition can include Compound 1 in an amount of about 0.1% w/v, or 0.2, 0.3, 0.4, 0.5, 0.6, 0.7, 0.8, 0.9, or about 1% w/v, and cyclodextrin in an amount of about 6, 7, 8, 9, 10, 11, 12, 13, 14, 15, 16, 17, 18, 19, 20, 25, 30, 35, 40, 45, or 50% w/v. In some embodiments, the injectable composition includes Compound 1 in an amount of 0.1% to 10% w/v, and cyclodextrin in an amount of 5% to 50% w/v. In some embodiments, the injectable composition includes Compound 1 in an amount of 0.1% to 1% w/v, and cyclodextrin in an amount of 10% to 20% w/v. In some embodiments, the injectable composition includes Compound 1 in an amount of about 0.5% w/v, and cyclodextrin in an amount of about 15% w/v. In some embodiments, the injectable composition includes Compound 1 in an amount of about 0.5% w/v, and betadex-sulfobutylether sodium in an amount of about 15% w/v.

In some embodiments, the injectable composition includes Compound 1 in an amount of 0.1% to 10% w/v, cyclodextrin in an amount from 10% to 20% w/v, and water safe for injection. In some embodiments, the injectable composition includes Compound 1 in an amount of about 0.5% w/v, cyclodextrin in an amount of about 15% w/v, and water safe for injection. In some embodiments, the injectable composition consists essentially of Compound 1 in an amount of about 0.5% w/v, cyclodextrin in an amount of about 15% w/v, and water safe for injection.

In some embodiments, the injectable composition includes Compound 1 in an amount of 0.1% to 10% w/v, betadex-sulfobutylether sodium in an amount from 10% to 20% w/v, and water safe for injection. In some embodiments, the injectable composition includes Compound 1 in an amount of about 0.5% w/v, betadex-sulfobutylether sodium in an amount of about 15% w/v, and water safe for injection. In some embodiments, the injectable composition consists essentially of Compound 1 in an amount of about 0.5% w/v, betadex-sulfobutylether sodium in an amount of about 15% w/v, and water safe for injection.

The injectable composition can be contained in any suitable container, such as a sealed vial. In some embodiments, the present invention provides a sealed vial containing the injectable composition. In some embodiments, the present invention provides a sealed vial containing the injectable composition consisting essentially of Compound 1 in an amount of about 0.5% w/v, cyclodextrin in an amount of about 15% w/v, and water safe for injection.

IV. Methods of Treating

In some embodiments, the present invention provides a method of treating a viral infection comprising administering a pharmaceutical composition comprising Compound 1, or a pharmaceutically acceptable salt thereof, cyclodextrin, and, optionally, pH adjusting agents. In some embodiments, the pharmaceutical composition is a composition of the present invention.

In some embodiments, the present invention provides a method of treating a viral infection comprising administering a pharmaceutical composition comprising Compound 1, or a pharmaceutically acceptable salt thereof, and beta-cyclodextrin, and, optionally, pH adjusting agents. In some embodiments, the pharmaceutical composition is a composition of the present invention.

In some embodiments, the present invention provides a method of treating a viral infection comprising parenterally administering a pharmaceutical composition comprising Compound 1, or a pharmaceutically acceptable salt thereof, and beta-cyclodextrin, and, optionally, pH adjusting agents. In some embodiments, the pharmaceutical composition is a composition of the present invention.

In some embodiments, the present invention provides a method of treating a viral infection comprising (a) reconstituting with safe water for injection a lyophilized pharmaceutical composition comprising Compound 1, or a pharmaceutically acceptable salt thereof, and beta-cyclodextrin, and, optionally, pH adjusting agents and (b) administering the reconstituted pharmaceutical composition. In some embodiments, the pharmaceutical composition is a composition of the present invention. In some embodiments, the reconstituted pharmaceutical composition is an injectable composition of the present invention. In some embodiments, the lyophilized pharmaceutical composition is a lyophilized composition of the present invention.

In some embodiments, the present invention provides a method of treating a viral infection comprising (a) reconstituting with safe water for injection a lyophilized pharmaceutical composition comprising Compound 1, or a pharmaceutically acceptable salt thereof, and beta-cyclodextrin, and, optionally, pH adjusting agents and (b) parenterally administering the reconstituted pharmaceutical composition. In some embodiments, the pharmaceutical composition is a composition of the present invention. In some embodiments, the reconstituted pharmaceutical composition is an injectable composition of the present invention. In some embodiments, the lyophilized composition is a lyophilized pharmaceutical composition of the present invention.

In some embodiments, the parenteral administration is selected from the group consisting of intramuscular (IM), subcutaneous (SC) and intravenous (IV) administrations.

In some embodiments, the present invention provides a method of treating a virus comprising parenterally administering a pharmaceutical composition comprising Compound 1, or a pharmaceutically acceptable salt thereof, and beta-cyclodextrin, and, optionally, pH adjusting agents. In some embodiments, the present invention provides a method of treating a virus comprising parenterally administering a pharmaceutical composition comprising Compound 1, or a pharmaceutically acceptable salt thereof, and beta-cyclodextrin, and, optionally, pH adjusting agents, wherein the virus is an Arenaviridae virus, a Coronaviridae virus, a Filoviridae virus, a Flaviviridae virus or a Paramyxoviridae virus. In some embodiments, the present invention provides a method of treating a virus comprising parenterally administering a pharmaceutical composition comprising Compound 1, or a pharmaceutically acceptable salt thereof, and beta-cyclodextrin, and, optionally, pH adjusting agents, wherein the virus is Lassa, Junin, Severe Acute Respiratory Syndrome (SARS), Middle Eastern Respiratory Syndrome (MERS), ebolavirus, Marburg virus, Zika, or Respiratory Syncytial virus. In some embodiments, the present invention provides a method of treating a virus comprising parenterally administering a pharmaceutical composition comprising Compound 1, or a pharmaceutically acceptable salt thereof, and beta-cyclodextrin, and, optionally, pH adjusting agents, wherein the virus is Lassa, Junin, Severe Acute Respiratory Syndrome (SARS), Middle Eastern Respiratory Syndrome (MERS), other human coronaviruses (229E, NL63, OC43, HKU1, or WIV1), zoonotic coronaviruses (PEDV or HKU CoV isolates such as HKU3, HKU5, or HKU9), ebolavirus (variants Zaire, Bundibugio, Sudan, Tai forest, or Reston), Marburg virus, Nipah, Hendra, Measles, Mumbs, Dengue, Yellow Fever, West Nile Virus, Zika, Parainfluenza, Metapneumovirus or Respiratory Syncytial virus.

In some embodiments, the present invention provides a method of treating a virus comprising parenterally administering a pharmaceutical composition comprising Compound 1, or a pharmaceutically acceptable salt thereof, and beta-cyclodextrin, and, optionally, pH adjusting agents, wherein the virus is ebolavirus.

Combination Therapies

In some embodiments, the present invention provides a method for treating an Arenaviridae virus, a Coronaviridae virus, a Filoviridae virus, a Flaviviridae virus or a Paramyxoviridae virus infection in a human comprising administering to the human a therapeutically effective amount of a composition disclosed herein in combination with a therapeutically effective amount of one or more (e.g., one, two, three, one or two, or one to three) additional therapeutic agents. In some embodiments, the present invention provides a method for treating an Arenaviridae virus infection in a human comprising administering to the human a therapeutically effective amount of a composition disclosed herein in combination with a therapeutically effective amount of one or more (e.g., one, two, three, one or two, or one to three) additional therapeutic agents. In some embodiments, the present invention provides a method for treating a Coronaviridae virus infection in a human comprising administering to the human a therapeutically effective amount of a composition disclosed herein in combination with a therapeutically effective amount of one or more (e.g., one, two, three, one or two, or one to three) additional therapeutic agents. In some embodiments, the present invention provides a method for treating a Filoviridae virus infection in a human comprising administering to the human a therapeutically effective amount of a composition disclosed herein in combination with a therapeutically effective amount of one or more (e.g., one, two, three, one or two, or one to three) additional therapeutic agents. In some embodiments, a method for treating a Flaviviridae virus infection in a human comprising administering to the human a therapeutically effective amount of a composition disclosed herein in combination with a therapeutically effective amount of one or more (e.g., one, two, three, one or two, or one to three) additional therapeutic agents. In some embodiments, the present invention provides a method for treating a Paramyxoviridae virus infection in a human comprising administering to the human a therapeutically effective amount of a composition disclosed herein in combination with a therapeutically effective amount of one or more (e.g., one, two, three, one or two, or one to three) additional therapeutic agents.

In some embodiments, the additional therapeutic agent used in combination with a compound disclosed herein is active against an Arenaviridae virus, a Coronaviridae virus, a Filoviridae virus, a Flaviviridae virus or a Paramyxoviridae virus infections. Non-limiting examples of these other active therapeutic agents are ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), and rVSV-EBOV, and mixtures thereof. The compounds and compositions of the present invention may also be used in combination with phosphoramidate morpholino oligomers (PMOs), which are synthetic antisense oligonucleotide analogs designed to interfere with translational processes by forming base-pair duplexes with specific RNA sequences. Examples of PMOs include AVI-7287, AVI-7288, AVI-7537, AVI-7539, AVI-6002, and AVI-6003.

In some embodiments, the present invention provides a method of treating a Filoviridae virus infections comprising administering a composition comprising Compound 1, or a pharmaceutically acceptable salt thereof, cyclodextrin, and, optionally, pH adjusting agents, in combination with an additional therapeutic agent wherein the additional therapeutic agent is ZMapp.

Co-administration of a composition disclosed herein with a therapeutically effective amount of a one or more additional therapeutic agents generally refers to simultaneous or sequential administration of a compound disclosed herein and one or more additional therapeutic agents, such that the composition disclosed herein and the one or more additional therapeutic agents are both present in the body of the patient.

Co-administration includes administration of unit dosages comprising a therapeutically effective amount of one or more compositions disclosed herein before or after administration of unit dosages of a therapeutically effective amount of one or more additional therapeutic agents, for example, administration of the compositions disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

V. Methods of Preparing

The compositions of the present invention can be prepared by means generally known to one of skill in the art for removing water from a substance. For example, the compositions can be dehydrated by heating the sample to a suitable temperature for a suitable period of time. The compositions can also be dehydrated under a reduced pressure atmosphere at any suitable temperature. The reduced pressure atmosphere can be any pressure less than atmospheric pressure. The reduced pressure atmosphere can be heated to a temperature above room temperature, be maintained at about room temperature, or cooled to a temperature below room temperature. For example, the compositions can be cooled to a temperature of less than room temperature while under a reduced pressure atmosphere. Suitable temperatures include, but are not limited to, less than room temperature, or less than 20° C., 15, 10, 5, 0, −5, −10, −15, −20, −25, −30, −40, or less than −50° C. When a reduced pressure atmosphere is used, the reduced pressure atmosphere can be less than atmospheric pressure, or less than 100 torr (mm Hg), 50, 25, 10, 5, 4.58 (the triple point for water), 4, 3, 2, 1, 0.5, 0.1, 0.05, or less than 0.01 torr. The compositions can be cooled to a temperature of less than 0.01° C. while under a reduced pressure atmosphere of less than 4.58 torr (611 Pascal or 0.006 atmospheres).

The compositions of the present invention can be prepared according to the methods described in the examples below and variations thereof understood by one of skill in the art. For example, the lyophilized composition of the present invention can be prepared by dissolving cyclodextrin in water, acidifying the cyclodextrin mixture to a pH of less than 2, adding Compound 1 to the acidified mixture to form a suspension of the complex of Compound 1 and the cyclodextrin, adjusting the pH of the complexed mixture as needed to a pH of about 2 to form a solution of the complex of Compound 1 and the cyclodextrin, adjusting the pH of the solution to about 3.5 to form a supersaturated solution, adding water to the supersaturated solution as needed to form a mixture wherein the Compound 1 is at a concentration of about 6.7 mg/mL and the cyclodextrin is at a concentration of about 20% w/v, and lyophilizing the mixture. In some embodiments, the present invention provides a method of preparing a lyophilized composition including Compound 1:

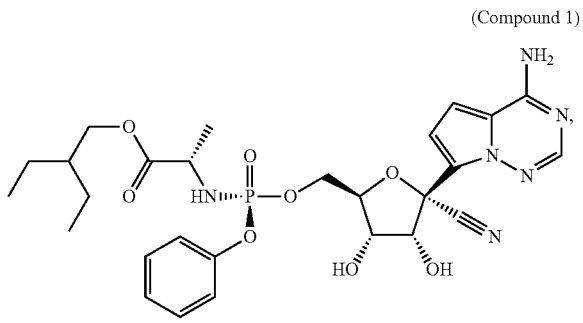 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

(Compound 1)

or a pharmaceutically acceptable salt thereof, and cyclodextrin, wherein the method includes forming a first mixture comprising cyclodextrin and water, such that the cyclodextrin dissolves; adding acid to the first mixture to form a second mixture having a pH of less than 2; adding Compound 1 to the second mixture, to form a third mixture; optionally adding acid or base to the third mixture to form a fourth mixture having a pH of from 3 to 4; and lyophilizing the third or fourth mixture to form the lyophilized composition.

Compound 1

Compound 1 can be used in any suitable amount to achieve the desired concentration in mixture prior to lyophilization. For example, Compound 1 can be present in an amount of 1 mg to 1000 mg, or 5 to 500, or 50 to 250, or 60 to 240, or 70 to 230, or 80 to 220, or 90 to 210, or 100 to 200, or 90 to 110, or 145 to 165, or 90 mg to 175 mg. Compound 1 can also be present in an amount of about 10 mg, or about 20, 30, 40, 50, 60, 70, 80, 90, 100, 110, 120, 130, 140, 150, 160, 170, 180, 190, 200, 210, 220, 230, 240, or about 250 mg. In some embodiments, the mixture includes 90 mg to 175 mg of Compound 1. In some embodiments, the mixture includes 100 mg of Compound 1. In some embodiments, the mixture includes 150 mg of Compound 1.

In some embodiments, Compound 1 is present in the third or fourth mixture at about 1 to 10 mg/mL. In some embodiments, Compound 1 is present at about 4 to 8 mg/mL. In some embodiments, Compound 1 is present at about 5 to 7 mg/mL. In some embodiments, Compound 1 is present at about 5 mg/mL. In some embodiments, Compound 1 is present at about 6.7 mg/mL. In some embodiments, Compound 1 is present in the fourth mixture at about 6.7 mg/mL. In some embodiments, Compound 1 is present at 5.0 mg/mL. In some embodiments, Compound 1 is present at 6.7 mg/mL. In some embodiments, Compound 1 is present in the fourth mixture at 6.7 mg/mL.

Compound 1 can be of any suitable form. For example, Compound 1 can be amorphous or crystalline. In some embodiments, Compound 1 is amorphous Compound 1. Crystalline forms of Compound 1 useful in the methods and compositions of the present invention are described in U.S. application Ser. No. 15/964,597. For example, Compound 1 can be crystalline Form I, Form II, Form III or Form IV. In some embodiments, Compound 1 is crystalline Compound 1.

In some embodiments, Compound 1 is crystalline Compound 1 Form II. In some embodiments, crystalline Compound 1 is characterized by an X-ray powder diffraction (XRPD) pattern having at least three peaks selected from the group consisting of 22.3°, 16.2°, 22.5°, 13.8°, 12.7°, 16.9°, 10.6°, 14.5°, 24.3, 24.0°, 17.6°, 23.4°, 8.1°, 11.0°, 26.8°, 28.9°, 19.6°, 27.8°, 26.4°, 28.7°, 29.8°, 33.0°, 18.8°, 183°, 32.1°, 25.3°, 32.6°, 8.6°, 342°, 35.9°, 27.2°, 28.1°, 38.9°, 34.6°, 17.1°, 35.2°, 21.4°, 30.6°, 25.6°, 18.5°, 31.7°, 36.5°, and 37.1°±0.2° 2-θ.

In some embodiments, crystalline Compound 1 Form II has an XRPD pattern comprising degree 2θ-reflections (+/−0.2 degrees 2θ) at 22.3°, 16.9°, and 16.2°. In some embodiments, crystalline Compound 1 Form II has an XRPD pattern comprising degree 2θ-reflections (+/−0.2 degrees 2θ) at 22.3°, 16.9°, and 16.2° and one or more of the degree 2θ-reflections (+/−0.2 degrees 2θ) at 13.8° and 12.7°. In some embodiments, crystalline Compound 1 Form II has an XRPD pattern comprising degree 2θ-reflections (+/−0.2 degrees 2θ) at 22.3°, 16.9°, and 16.2° and one of the degree 2θ-reflections (+/−0.2 degrees 2θ) at 13.8° and 12.7°. In some embodiments, crystalline Compound 1 Form II has an XRPD pattern comprising degree 2θ-reflections (+/−0.2 degrees 2θ) at 22.3°, 16.9°, and 16.2° and two of the degree 2θ-reflections (+/−0.2 degrees 2θ) at 13.8° and 12.7°. In some embodiments, crystalline Compound 1 Form II has an XRPD pattern comprising degree 2θ-reflections (+/−0.2 degrees 2θ) at 22.3°, 16.9°, 16.2°, 13.8° and 12.7°. In some embodiments, crystalline Compound 1 Form II has an XRPD pattern comprising any three degree 2θ-reflections (+/−0.2 degrees 2θ) selected from the group consisting of 22.3°, 16.9°, 16.2°, 13.8°, and 12.7°.

In some embodiments, crystalline Compound 1 Form II has an XRPD pattern further comprising degree 2θ-reflections (+/−0.2 degrees 2θ) at 22.5°, 10.6° and 14.5°. In some embodiments, crystalline Compound 1 Form II has an XRPD pattern comprising degree 2θ-reflections (+/−0.2 degrees 2θ) at 22.3°, 16.9°, 16.2°, 13.8° and 12.7° and one or more of the degree 2θ-reflections (+/−0.2 degrees 2θ) at 22.5°, 10.6° and 14.5°. In some embodiments, crystalline Compound 1 Form II has an XRPD pattern comprising degree 2θ-reflections (+/−0.2 degrees 2θ) at 22.3°, 16.9°, 16.2°, 13.8° and 12.7° and one of the degree 2θ-reflections (+/−0.2 degrees 2θ) at 22.5°, 10.6° and 14.5°. In some embodiments, crystalline Compound 1 Form II has an XRPD pattern comprising degree 2θ-reflections (+/−0.2 degrees 2θ) at 22.3°, 16.9°, 16.2°, 13.8° and 12.7° and two of the degree 2θ-reflections (+/−0.2 degrees 2θ) at 22.5°, 10.6° and 14.5°. In some embodiments, crystalline Compound 1 Form II has an XRPD pattern comprising degree 2θ-reflections (+/−0.2 degrees 2θ) at 22.3°, 16.9°, 16.2°, 13.8°, 12.7°, 22.5°, 10.6° and 14.5°. In some embodiments, crystalline Compound 1 Form II has an XRPD pattern comprising any three degree 2θ-reflections (+/−0.2 degrees 2θ) selected from the group consisting of 22.3°, 16.9°, 16.2°, 13.8°, 12.7°, 22.5°, 10.6° and 14.5°.

Compound 1 can have any suitable purity. For example, the compound of Formula I can have a purity of at least 90%, or at least 91, 92, 93, 94, 95, 96, 97, 98, 99, or at least 99.1, 99.2, 99.3, 99.4, 99.5, 99.6, 99.7, 99.8 or at least 99.9%. In some embodiments, Compound 1 has a purity of at least 99.1%. In some embodiments, Compound 1 has a purity of at least 99.3%. In some embodiments, Compound 1 has a purity of at least 99.5%. In some embodiments, Compound 1 has a purity of at least 99.7%.

The impurities present in Compound 1 can include unreacted starting material, undesirable side-products, and other materials. Representative impurities include Impurity A:

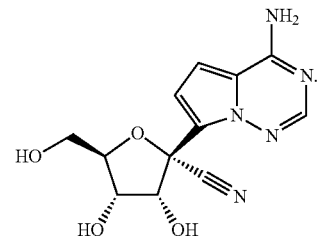

Impurity A can be present in an amount less than about 0.5%, or less than about 0.45%, 0.40, 0.35, 0.30, 0.25, 0.20, 0.15, 0.10, 0.09, 0.08, 0.07, 0.06, 0.05, 0.04, 0.03, 0.02, or less than about 0.01%. The amount of Impurity A can be measured in % AN as measured by HPLC, or can be based on weight (w/w). In some embodiments, Compound 1 includes less than 0.10% Impurity A. In some embodiments, Compound 1 includes less than 0.05% Impurity A.

In some embodiments, Compound 1 can have a purity of at least 99.1%, and include less than 0.10% Impurity A. In some embodiments, Compound 1 can have a purity of at least 99.1%, and include less than 0.05% Impurity A. In some embodiments, Compound 1 can have a purity of at least 99.1%, and include less than 0.04% Impurity A. In some embodiments, Compound 1 can have a purity of at least 99.5%, and include less than 0.04% Impurity A. In some embodiments, Compound 1 can have a purity of at least 99.5%, and include less than 0.04% Impurity A.

Cyclodextrin

The cyclodextrin can include any suitable cyclodextrin as described above. For example, the cyclodextrin can be a beta-cyclodextrin, such as sulfobutylalkylether-beta-cyclodextrin, betadex-sulfobutylether sodium, or hydroxypropyl-beta-cyclodextrin. In some embodiments, the cyclodextrin includes a beta-cyclodextrin. In some embodiments, the cyclodextrin includes sulfobutylalkylether-beta-cyclodextrin, betadex-sulfobutylether sodium, or hydroxypropyl-beta-cyclodextrin. In some embodiments, the cyclodextrin includes betadex-sulfobutylether sodium.

The cyclodextrin can be present in any suitable amount. For example, the cyclodextrin can be present in the mixture at 1 to 50% w/v, or 5 to 30, or 10 to 25, or 14% to 21% w/v. The cyclodextrin can also be present in the mixture at about 1% w/v, or 5, 10, 11, 12, 13, 14, 15, 16, 17, 18, 19, 20, 21, 22, 23, 24, 25, 30, 35, 40, 45 or about 50% w/v. In some embodiments, the cyclodextrin is present at 5% to 30% w/v. In some embodiments, the cyclodextrin is present at 10% to 25% w/v. In some embodiments, the cyclodextrin is present at 14% to 21% w/v. In some embodiments, the cyclodextrin is present at about 15% w/v. In some embodiments, the cyclodextrin is present at about 20% w/v. In some embodiments, the cyclodextrin is present at 15% w/v. In some embodiments, the cyclodextrin is present at 20% w/v.

In some embodiments, the beta-cyclodextrin is present at about 5% to 30% w/v. In some embodiments, the beta-cyclodextrin is present at 10% to 25% w/v. In some embodiments, the beta-cyclodextrin is present at 14% to 21% w/v. In some embodiments, the beta-cyclodextrin is present at about 15% w/v. In some embodiments, the beta-cyclodextrin is present at about 20% w/v. In some embodiments, the beta-cyclodextrin is present at 15% w/v. In some embodiments, the beta-cyclodextrin is present at 20% w/v.

pH Adjusting Agents

The pH adjusting agents useful in the methods of the present invention include any suitable acid and/or base. Representative acids include mineral acids such as hydrofluoric acid, hydrochloric acid, hydrobromice acid, etc. In some embodiments, the acid is hydrochloric acid. Other acids are useful in the methods of the present invention and are described above.

Representative bases include hydroxides such as lithium hydroxide, sodium hydroxide, potassium hydroxide, rubidium hydroxide, cesium hydroxide, magnesium hydroxide, strontium hydroxide, barium hydroxide, and others. In some embodiments, the base is sodium hydroxide. Other bases are useful in the methods of the present invention and are described above.

The pH adjusting agents can be used in any suitable amount to adjust the pH of the mixture to achieve the target pH.

In some embodiments, the mixture includes Compound 1, or a pharmaceutically acceptable salt thereof, and beta-cyclodextrin, and, optionally, pH adjusting agents, wherein Compound 1 is present at about 4.0 to 8.0 mg/mL and the beta-cyclodextrin is present at about 5% to 30% w/v. In some embodiments, the mixture includes Compound 1, or a pharmaceutically acceptable salt thereof, and beta-cyclodextrin, and, optionally, pH adjusting agents, wherein Compound 1 is present at about 4.0 to 8.0 mg/mL and the beta-cyclodextrin is present at about 10% to 25% w/v. In some embodiments, the mixture includes Compound 1, or a pharmaceutically acceptable salt thereof, and beta-cyclodextrin, and, optionally, pH adjusting agents, wherein Compound 1 is present at about 4.0 to 8.0 mg/mL and the beta-cyclodextrin is present at about 14% to 21% w/v.

In some embodiments, the mixture includes Compound 1, or a pharmaceutically acceptable salt thereof, and beta-cyclodextrin, and, optionally, pH adjusting agents, wherein Compound 1 is present at about 5.0 to 7.0 mg/mL and the beta-cyclodextrin is present at about 5% to 30% w/v. In some embodiments, the mixture includes Compound 1, or a pharmaceutically acceptable salt thereof, and beta-cyclodextrin, and, optionally, pH adjusting agents, wherein Compound 1 is present at about 5.0 to 7.0 mg/mL and the beta-cyclodextrin is present at about 10% to 25% w/v. In some embodiments, the mixture includes Compound 1, or a pharmaceutically acceptable salt thereof, and beta-cyclodextrin, and, optionally, pH adjusting agents, wherein Compound 1 is present at about 5.0 to 7.0 mg/mL and the beta-cyclodextrin is present at about 14% to 21% w/v.

In some embodiments, the mixture includes Compound 1, or a pharmaceutically acceptable salt thereof, and beta-cyclodextrin, and, optionally, pH adjusting agents, wherein Compound 1 is present at about 5.0 mg/mL and the beta-cyclodextrin is present at about 15% w/v. In some embodiments, the mixture includes Compound 1, or a pharmaceutically acceptable salt thereof, and beta-cyclodextrin, and, optionally, pH adjusting agents, wherein Compound 1 is present at about 6.7 mg/mL and the beta-cyclodextrin is present at about 20% w/v.

In some embodiments, a vial comprising Compound 1, or a pharmaceutically acceptable salt thereof, and beta-cyclodextrin, and, optionally, pH adjusting agents, wherein Compound 1 is present at about 5.0 mg/mL and the beta-cyclodextrin is present at about 15% w/v further comprising water for injection. In some embodiments, a vial comprising Compound 1, or a pharmaceutically acceptable salt thereof, and beta-cyclodextrin, and, optionally, pH adjusting agents, wherein Compound 1 is present at about 6.7 mg/mL and the beta-cyclodextrin is present at about 20% w/v further comprising water for injection.

In some embodiments, the mixture includes about 90 to 175 mg Compound 1, or a pharmaceutically acceptable salt thereof, and beta-cyclodextrin, and, optionally, pH adjusting agents, wherein the beta-cyclodextrin is present at about 15 to 20% w/v. In some embodiments, the mixture includes about 100 mg Compound 1, or a pharmaceutically acceptable salt thereof, and beta-cyclodextrin, and, optionally, pH adjusting agents, wherein the beta-cyclodextrin is present at about 15 to 20% w/v. In some embodiments, the mixture includes about 150 mg Compound 1, or a pharmaceutically acceptable salt thereof, and beta-cyclodextrin, and, optionally, pH adjusting agents, wherein the beta-cyclodextrin is present at about 15 to 20% w/v.

Process Conditions

The pH of the second mixture can be any suitable pH less than 2. For example, the pH of the second mixture can be less than 2, or 1.95, 1.9, 1.85, 1.8, 1.75, 1.7, 1.65, 1.6, or less than 1.5. The pH of the second mixture can be about 1.95, 1.9, 1.85, 1.8, 1.75, 1.7, 1.65, 1.6, or about 1.5. In some embodiments, the second mixture has a pH of about 1.75.

The pH of the third or fourth mixture can be any suitable pH from 3 to 4. For example, the pH of the third or fourth mixture can be about 3.1, 3.2, 3.3, 3.4, 3.5, 3.6, 3.7, 3.8, or about 3.9. In some embodiments, the fourth mixture has a pH of 3 to 4. In some embodiments, the fourth mixture has a pH of about 3.5.

In some embodiments, the method of preparing a lyophilized composition includes forming the first mixture comprising cyclodextrin and water, such that the cyclodextrin dissolves; adding acid to the first mixture to form a second mixture having a pH of less than 2; adding Compound 1 to the second mixture such that Compound 1 dissolves, to form the third mixture; adding base to the third mixture to form the fourth mixture having a pH of from 3 to 4; and lyophilizing the fourth mixture to form the lyophilized composition.

In some embodiments, the method of preparing a lyophilized composition includes forming the first mixture comprising betadex-sulfobutylether sodium and water, such that the betadex-sulfobutylether sodium dissolves; adding hydrochloric acid to the first mixture to form a second mixture having a pH of less than 2; adding Compound 1 to the second mixture such that Compound 1 dissolves, to form the third mixture; adding sodium hydroxide to the third mixture to form the fourth mixture having a pH of about 3.5; and lyophilizing the fourth mixture to form the lyophilized composition.

In some embodiments, the method of preparing a lyophilized composition includes forming the first mixture comprising betadex-sulfobutylether sodium and water, such that the betadex-sulfobutylether sodium dissolves; adding hydrochloric acid to the first mixture to form a second mixture having a pH of less than 2; adding a crystalline form of Compound 1 to the second mixture such that Compound 1 dissolves, to form the third mixture; adding sodium hydroxide to the third mixture to form the fourth mixture having a pH of about 3.5, wherein the fourth mixture is a supersaturated solution of Compound 1; and lyophilizing the fourth mixture to form the lyophilized composition.

In some embodiments, the method includes forming the first mixture comprising betadex-sulfobutylether sodium and water; adding hydrochloric acid to the first mixture to form the second mixture having a pH of less than 2; adding the crystalline form of Compound 1 in the second mixture, to form the third mixture; adding sodium hydroxide to the third mixture to form the fourth mixture having a pH of about 3.5; adding water to the fourth mixture such that Compound 1 is present at about 6.7 mg/mL and betadex-sulfobutylether sodium is present at about 20% w/v; and lyophilizing the fourth mixture to form the composition.

Betadex sulfobutyl ether sodium was dissolved in a suitable amount of water for injection in a suitable mixing vessel. The bulk solution was acidified by addition of HCl. Compound 1 was then added and the pH reduced with additional HCl and/or NaOH to facilitate Compound 1 dissolution. The pH of the bulk solution was then adjusted to a range of 3 to 4 by addition of HCl and/or NaOH to obtain an aqueous solution containing a supersaturated solution of Compound 1. Water for injection was then added to the solution to obtain the desired concentration of Compound 1 for vial filling followed by additional pH adjustment with HCl and/or NaOH if necessary. The solution was then sterilized via filtration and aseptically filled into glass vials and lyophilized to obtain a lyophilized powder for reconstitution.

VI. Methods of Use

The use of beta cyclodextrin derivatives in formulating certain medicinal agents to improve solubility, safety and other parameters has been disclosed in, for example, U.S. Pat. Nos. 5,134,127, 5,376,645, 7,635,773, 7,625,878, and 8,410,077 the entirety of each of which is incorporated herein by reference. Prior to applicants' disclosure, the difficulty of preparing an IV solution of Compound 1 was unknown. Prior to applicants' disclosure the type of solubilizing agent(s) useful to achieve an effective IV formulation comprising Compound 1 was unknown. Applicants have surprisingly discovered that the use of beta-cyclodextrin derivatives is useful to achieve an effective IV solution of Compound 1. An IV solution of Compound 1 comprising a beta cyclodextrin derivative provides advantages of (1) ability to deliver varying required doses of Compound 1; (2) ability to adjust infusion rate without precipitation of Compound 1; (3) ability to avoid the problems associated with the use of other IV formulations such as the use of TWEEN® 80 or organic co-solvents.

As a result of the discovery disclosed herein, one of ordinary skill in the art is able to (1) prepare an IV solution of Compound 1 as a bolus solution (i.e. for direct use; or as a pre-concentrate for dilution prior to use in a human patient in need thereof). Thus, the present disclosure also provides the use of a kit comprising Compound 1 and a beta cyclodextrin derivative in an IV formulation for use in a human patient in need thereof. The kit may comprise a premixed large volume parenteral (LVP) or small volume parenteral SVP bag comprising Compound 1 and a beta cyclodextrin derivative. Alternatively, the kit may comprise an aqueous solution of a beta cyclodextrin (e.g. Captisol® or Dexolve-7®) and a vial of Compound 1 to be mixed on site or prior to use by one of ordinary skill in the art. The solution comprising a saline solution of a beta cyclodextrin e.g. Captisol® may need to be further diluted (e.g. use of about a 20-50% concentrate) by one of ordinary skill in the art prior to mixing to form an intravenous formulation for administration to a patient in need thereof. The present disclosure is thus directed to the preparation, manufacture and/or use of an intravenous formulation comprising Compound 1 and a beta cyclodextrin derivative for use in IV treatment. A preferred beta cyclodextrin derivative is Captisol®. Also preferred is the beta cyclodextrin derivative Dexolve-7®. Also preferred is the beta cyclodextrin derivative betadex sulfobutyl ether sodium. Thus, in some embodiments, the present disclosure provides a kit comprising Compound 1 and a beta-cyclodextrin derivative for the treatment of a Filoviridae virus infection in a patient in need thereof. The ultimate decision on dosing rate, concentration of beta cyclodextrin derivative solution to be dosed and duration thereof are to be made by a qualified caregiver.

VII. Examples

Example 1. Preparation of Lyophilized Composition

Aqueous

Having determined the water solubility of Compound 1 is low at about 0.03 mg/mL, exploration of dissolving 1 to 300 mg of Compound 1 in water or saline may be impractical for use in treating Arenaviridae, Coronaviridae, Filoviridae, Flaviviridae, or Paramyxoviridae viral infections.

Co-Solvents

In a co-solvent system, drug solubility decreases logarithmically as the percent of the solvent decreases linearly. Thus, there is potential for precipitation upon dilution, which may make a co-solvent system impractical for use in treating Arenaviridae, Coronaviridae, Filoviridae, Flaviviridae, or Paramyxoviridae viral infections.

Pre-Concentrate

Pre-concentrated formulations of a surfactant and an organic solvent (pre-concentrates) were explored. A solution formulation comprising Compound 1 present in about 30 mg/mL in 25% TWEEN® 80, 50% PEG 300, and 25% water was evaluated, but showed precipitation upon 10× and 100× dilution in normal saline. Other explored formulations included solution formulations comprising Compound 1 present in about 5 mg/mL in 25% Tween 80, 25% PEG 300, 50% water and another solution formulation comprising Compound 1 present at about 5 mg/mL in 25% TWEEN® 80, 75% water. These other formulations did not exhibit precipitation upon dilution in normal saline, but would require larger amounts of TWEEN® 80 which could be associated with toxicity.

Complexation

Complexation with a beta-cyclodextrin derivative was explored successfully. In a solution that utilizes complexation with beta cyclodextrin derivative, the drug solubility decreases linearly (assuming a 1:1 complex) as the amount of cyclodextrin decreases linearly, limiting the potential for precipitation of Compound 1 upon dilution.

However, in another experiment, 4.5 g of betadex sulfobutyl ether sodium was dissolved in a suitable amount of water for injection in a suitable mixing vessel. The bulk solution was acidified to a pH less than 2 by the addition of HCl to facilitate dissolution of Compound 1 and complexation with betadex sulfobutyl ether sodium. A crystalline form of Compound 1 (150 mg) was added. To make the pH more neutral to between 3 and 4, NaOH was added. Surprisingly, upon addition of NaOH, Compound 1 and betadex sulfobutyl ether sodium remained complexed. When molecules are complexed under an acidic condition, increasing the pH can result in weakened or broken complexation. However, complexation between Compound 1 and betadex sulfobutyl ether sodium was maintained, forming a supersaturated solution. After complexation and pH adjusting, the solution was sterilized via filtration and aseptically filled into glass vials having a concentration for Compound 1 of 6.7 mg/mL and 20% w/v for betadex sulfobutyl ether sodium. The mixture was lyophilized to obtain a lyophilized powder for reconstitution, having 3.23% (w/w) Compound 1 and 96.77% (w/w) betadex-sulfobutylether sodium.

Stability Testing

Lyophilized drug product vials were placed into temperature and humidity controlled chambers for predefined time intervals and removed for testing. The drug product vials were tested using analytical methods determined to be stability indicating such as liquid chromatography to monitor product purity.

TABLE 1

18-Month Stability Data for Lyophilized Composition

| TEST | T = 0 | 18 Months 25° C./ 60% RH | 30° C./ 75% RH | 6 Months 40° C./ 75% RH |
|---|---|---|---|---|
| pH | 3.7 | 3.6 | 3.6 | 3.6 |
| Strength (%) | 100.0 | 100.1 | 100.3 | 99.2 |
| Deg Product Content (%) | 0.0 | 0.2 | 0.2 | 0.3 |
| Water Content | 1.9 | 1.5 | 1.6 | 1.7 |
| Impurity A | 0.10 (Trace) | 0.10 | 0.10 | 0.10 |
| Impurity B | 0.08 (Trace) | 0.11 | 0.14 | 0.15 |

* ND < 0.05%.

Example 2. Preparation of Injectable Composition

The lyophilized composition of Example 1, was reconstituted with 29 mL of sterile water for injection, to prepare a 5 mg/mL composition having 0.5% (w/v) of Compound 1 and 15% (w/v) of betadex-sulfobutylether sodium. The reconstituted solution was diluted into intravenous infusion fluids prior to intravenous infusion.

TABLE 2

24-Month Stability Data for Injectable Composition

| TEST | T = 0 | 24 M −20° C. | 12 M 5° C. | 6 M 25° C./60% RH |
|---|---|---|---|---|
| pH | 3.5 | 3.5 | 3.5 | 3.5 |
| Strength (%) | 98.8 | 97.4 | 96.5 | 88.3 |
| Impurity Content (%) | 0.5 | 0.5 | 1.6 | 8.6 |
| Particulate Matter | <657 <171 | <657 <171 | <657 <171 | <657 <171 |
| Impurity A | ND | ND | 0.07 (Trace) | 0.52 |
| Impurity B | ND | 0.06 (Trace) | 1.11 | 6.88 |

* ND < 0.05%.

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application. Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. A composition comprising
(i) a Compound 1 in an amount of from 1% to 10% w/w

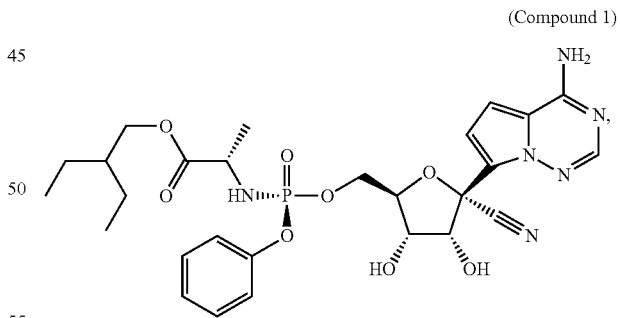

(Compound 1)

or a pharmaceutically acceptable salt thereof, and
(ii) cyclodextrin in an amount of from 90% to 99% w/w;
wherein the composition is a lyophilized composition.

2. The composition of claim 1, wherein the cyclodextrin is a beta-cyclodextrin.

3. The composition of claim 2, wherein the beta-cyclodextrin is sulfobutylalkylether-beta-cyclodextrin, betadex-sulfobutylether sodium, or hydroxypropyl-beta-cyclodextrin.

4. The composition of claim 2, wherein the beta-cyclodextrin is betadex-sulfobutylether sodium.

5. The composition of claim 1, comprising
(i) the Compound 1 in an amount of from 1% to 5% w/w; and
(ii) the cyclodextrin in an amount of from 95% to 99% w/w.

6. The composition of claim 5, wherein the cyclodextrin is betadex-sulfobutylether sodium.

7. The composition of claim 1, comprising
(i) the Compound 1 in an amount of from 2% to 4% w/w; and
(ii) the cyclodextrin in an amount of from 96% to 98% w/w.

8. The composition of claim 7, wherein the cyclodextrin is betadex-sulfobutylether sodium.

9. The composition of claim 1, comprising
(i) the Compound 1 in an amount of from 3% to 3.5% w/w; and
(ii) the cyclodextrin in an amount of from 96.5% to 97% w/w.

10. The composition of claim 9, wherein the cyclodextrin is betadex-sulfobutylether sodium.

11. The composition of claim 10, that is contained in a sealed vial.

12. The composition of claim 1, consisting essentially of the Compound 1 in an amount of 3.2% w/w, and the cyclodextrin betadex-sulfobutylether sodium in an amount of 96.8% w/w.

\* \* \* \* \*

UNITED STATES PATENT AND TRADEMARK OFFICE
CERTIFICATE OF CORRECTION

PATENT NO. : 10,675,296 B2
APPLICATION NO. : 16/031620
DATED : June 9, 2020
INVENTOR(S) : Larson et al.

It is certified that error appears in the above-identified patent and that said Letters Patent is hereby corrected as shown below:

On the Title Page

Under item (12), "Larson" should read --Larson et al.--

Item (72), Inventor: add --Robert G. Strickley, San Mateo, CA (US)--

Signed and Sealed this
Fifteenth Day of February, 2022

Drew Hirshfeld
*Performing the Functions and Duties of the
Under Secretary of Commerce for Intellectual Property and
Director of the United States Patent and Trademark Office*